United States Patent
Georgescu et al.

(10) Patent No.: US 12,094,182 B2
(45) Date of Patent: Sep. 17, 2024

(54) NEURAL NETWORK BASED IDENTIFICATION OF AREAS OF INTEREST IN DIGITAL PATHOLOGY IMAGES

(71) Applicant: Leica Biosystems Imaging Inc., Vista, CA (US)

(72) Inventors: Walter Georgescu, Vista, CA (US); Kiran Saligrama, Vista, CA (US); Allen Olson, Vista, CA (US); Girish Mallya Udupi, Vista, CA (US); Bruno Oliveira, Vista, CA (US)

(73) Assignee: Leica Biosystems Imaging Inc., Vista, CA (US)

( * ) Notice: Subject to any disclaimer, the term of this patent is extended or adjusted under 35 U.S.C. 154(b) by 176 days.

(21) Appl. No.: 17/416,394

(22) PCT Filed: May 29, 2020

(86) PCT No.: PCT/US2020/035302
§ 371 (c)(1),
(2) Date: Jun. 18, 2021

(87) PCT Pub. No.: WO2020/243556
PCT Pub. Date: Dec. 3, 2020

(65) Prior Publication Data
US 2022/0076411 A1  Mar. 10, 2022

Related U.S. Application Data

(60) Provisional application No. 62/854,040, filed on May 29, 2019, provisional application No. 62/854,130, filed on May 29, 2019.

(51) Int. Cl.
*G06V 10/44* (2022.01)
*G06T 7/00* (2017.01)
(Continued)

(52) U.S. Cl.
CPC .......... *G06V 10/454* (2022.01); *G06T 7/0012* (2013.01); *G06V 10/764* (2022.01);
(Continued)

(58) Field of Classification Search
CPC .... G06V 10/454; G06V 10/764; G06V 10/82; G06V 20/695; G06V 2201/03;
(Continued)

(56) References Cited

U.S. PATENT DOCUMENTS 10,049,447 B2 * 8/2018 Lloyd .................. G06F 18/24
2015/0213302 A1   7/2015 Madabhushi et al.
(Continued)

FOREIGN PATENT DOCUMENTS

WO   WO 2019/026081 A2   2/2019
WO   WO 2020/174863 A1   9/2020
WO   WO 2020/243556 A1   12/2020

OTHER PUBLICATIONS

Araújo, F.H., Silva, R.R., Ushizima, D.M., Rezende, M.T., Carneiro, C.M., Bianchi, A.G.C. and Medeiros, F.N., 2019. Deep learning for cell image segmentation and ranking. Computerized Medical Imaging and Graphics, 72, pp. 13-21.*

(Continued)

*Primary Examiner* — Zhitong Chen
(74) *Attorney, Agent, or Firm* — FROST BROWN TODD LLP

(57) ABSTRACT

A CNN is applied to a histological image to identify areas of interest. The CNN classifies pixels according to relevance classes including one or more classes indicating levels of interest and at least one class indicating lack of interest. The CNN is trained on a training data set including data which has recorded how pathologists have interacted with visualizations of histological images. In the trained CNN, the
(Continued)

in-terest-based pixel classification is used to generate a segmentation mask that defines areas of interest. The mask can be used to indicate where in an image clinically relevant features may be located. Further, it can be used to guide variable data compression of the histological image. Moreover, it can be used to control loading of image data in either a client-server model or within a memory cache policy. Furthermore, a histological image of a tissue sample of a tissue type that has been treated with a test compound is image processed in order to detect areas where toxic reactions to the test compound may have occurred. An autoencoder is trained with a training data set comprising histological images of tissue samples which are of the given tissue type, but which have not been treated with the test compound. The trained autoencoder is applied to detect tissue areas by their deviation from the normal variation seen in that tissue type as learnt by the training process, and so build up a toxicity map of the image. The toxicity map can then be used to direct a toxicological pathologist to examine the areas identified by the autoencoder as lying outside the normal range of heterogeneity for the tissue type. This makes the pathologist's review quicker and more reliable. The toxicity map can also be overlayed with the segmentation mask indicating areas of interest. When an area of interest and an area identified as lying outside the normal range of heterogeneity for the tissue type, and increased confidence score is applied to the overlapping area.

20 Claims, 12 Drawing Sheets

(51) Int. Cl.
  *G06V 10/764* (2022.01)
  *G06V 10/82* (2022.01)
  *G06V 20/69* (2022.01)
  *G16H 80/00* (2018.01)
(52) U.S. Cl.
  CPC ............ *G06V 10/82* (2022.01); *G06V 20/695* (2022.01); *G16H 80/00* (2018.01); *G06T 2207/10056* (2013.01); *G06T 2207/20084* (2013.01)
(58) Field of Classification Search
  CPC .............. G06V 2201/10; G06T 7/0012; G06T 2207/10056; G06T 2207/20084; G06T 7/11; G06T 2207/10024; G06T 2207/20021; G06T 2207/20081; G06T 2207/30096; G16H 80/00; G06N 3/08; G06N 3/045; G06F 18/2415
  See application file for complete search history.

(56) References Cited

U.S. PATENT DOCUMENTS

2019/0139270 A1  5/2019 DeFauw et al.
2019/0147592 A1  5/2019 Yu

OTHER PUBLICATIONS

Sharma, H., Zerbe, N., Klempert, I., Hellwich, O. and Hufnagl, P., 2017. Deep convolutional neural networks for automatic classification of gastric carcinoma using whole slide images in digital histopathology. Computerized Medical Imaging and Graphics, 61, pp. 2-13.*
Hou, L., Samaras, D., Kurc, T.M., Gao, Y., Davis, J.E. and Saltz, J.H., 2016. Patch-based convolutional neural network for whole slide tissue image classification. In Proceedings of the IEEE conference on computer vision and pattern recognition (pp. 2424-2433).*
International Search Report and Written Opinion mailed Oct. 29, 2020 for International App No. PCT/US2020/035302, in 18 pages.
Araújo, Flávio HD, et al. "Deep learning for cell image segmentation and ranking." *Computerized Medical Imaging and Graphics* 72 (2019): 13-21.
Bejnordi, Babak Ehteshami, et al. "Context-aware stacked convolutional neural networks for classification of breast carcinomas in whole-slide histopathology images." *Journal of Medical Imaging* 4.4 (2017): 044504-044504.
Cruz-Roa, Angel, et al. "Accurate and reproducible invasive breast cancer detection in whole-slide images: A Deep Learning approach for quantifying tumor extent." *Scientific reports* 7.1 (2017): 1-14.
Esteva, Andre, et al. "Dermatologist-level classification of skin cancer with deep neural networks." *nature* 542.7639 (2017): 115-118.
Hou, Le, et al. "Patch-based convolutional neural network for whole slide tissue image classification." *Proceedings of the IEEE conference on computer vision and pattern recognition*. 2016.
Liu, Yun, et al. "Detecting cancer metastases on gigapixel pathology images." *arXiv preprint arXiv:* 1703.02442 (2017).
Mobadersany, P., et al. "E. al.," Predicting cancer outcomes from histology and genomics using convolutional networks," PNAS 115." E2970-E2979 (2017).
Roa-Peña, Lucia, Francisco Gómez, and Eduardo Romero. "An experimental study of pathologist's navigation patterns in virtual microscopy." *Diagnostic pathology* 5 (2010): 1-11.
Schaumberg, Andrew J., et al. "DeepScope: nonintrusive whole slide saliency annotation and prediction from pathologists at the microscope." *Computational Intelligence Methods for Bioinformatics and Biostatistics: 13th International Meeting, CIBB 2016, Stirling, UK, Sep. 1-3, 2016, Revised Selected Papers 13*. Springer International Publishing, 2017.
Srivastava, Nitish, et al. "Dropout: a simple way to prevent neural networks from overfitting." *The journal of machine learning research* 15.1 (2014): 1929-1958.
Vandenberghe, Michel E., et al. "Relevance of deep learning to facilitate the diagnosis of HER2 status in breast cancer." *Scientific reports* 7.1 (2017): 1-11.
Wang, Dayong, et al. "Deep learning for identifying metastatic breast cancer." *arXiv preprint arXiv:* 1606.05718 (2016).
Liznerski, Philipp, et al. "Explainable deep one-class classification." *arXiv preprint arXiv:*2007.01760 (2020).
Extended European Search Report dated Dec. 8, 2023, for Application No. 23206311.5, 13 pages.
Japanese First Office Action dated Apr. 23, 2024, for Application No. 2021-538305, 3 pages.

\* cited by examiner

NEURAL NETWORK BASED IDENTIFICATION OF AREAS OF INTEREST IN DIGITAL PATHOLOGY IMAGES

BACKGROUND

Field of the Invention

The present disclosure relates to image processing of pathology images with a neural network in order to find areas of clinical interest and areas including toxicological pathology.

Related Art

Digital pathology continues to change the way pathologists view and diagnose slides. The traditional way for pathologists to examine a slide is to observe a glass slide under a microscope. The pathologist will start by viewing the slide with a low magnification objective. When an area with potential diagnostic value is observed, the pathologist will switch to a high magnification objective to look in more detail at that area. Subsequently, the pathologist will switch back to low magnification to continue examining other areas on the slide. This low-high-low magnification viewing sequence may be repeated several times over the slide until a definite and complete diagnosis can be made for the slide.

In the past twenty years, the introduction of digital scanners has changed this workflow. A digital scanner can acquire an image of an entire glass slide, a so-called whole slide image (WSI), and save it as a digital image data file in a largely automated process that does not need a pathologist. The resulting image data file is typically stored in a slide database from where it is available via a clinical network to a pathologist at a viewing workstation with a high-resolution display, the workstation having a visualization application for this purpose.

A more recent development in pathology is that CNN methods have become of increasing research interest. It is becoming increasingly reported that CNN methods are performing as well as, or even better than, pathologists in identifying and diagnosing tumors from pathology images.

Wang et al 2016 describes a CNN approach to detect metastasis of breast cancer to the lymph nodes.

US2015213302A1 describes how cellular mitosis is detected in a region of cancerous tissue. After training a CNN, classification is carried out based on an automated nuclei detection system which performs a mitotic count, which is then used to grade the tumor.

Hou et al 2016 processes brain and lung cancer images. Image patches from WSIs are used to make patch-level predictions given by patch-level CNNs.

Liu et al 2017 processes image patches extracted from a gigapixel breast cancer histology image with a CNN to detect and localize tumors by assigning a tumor probability to every pixel in the image.

Bejnordi et al 2017 applies two stacked CNNs to classify tumors in image patches extracted from WSIs of breast tissue stained with a hematoxylin and eosin (H&E) stain. The performance is shown to be good for object detection and segmentation in these pathology images. We further note that Bejnordi et al also provides an overview of other CNN-based tumor classification methods applied to breast cancer samples (see references 10-13).

Esteva et al 2017 applies a deep CNN to analyze skin lesions and classify the lesions according to a tree-structured taxonomy into various malignant types, non-malignant types and non-neoplastic types including the malignant types acrolentiginous melanoma, amelanotic melanoma and lentigo melanoma and the non-malignant types blue nevus, halo nevus and Mongolian spot. An image of a skin lesion (for example, melanoma) is sequentially warped into a probability distribution over clinical classes to perform the classification.

Mobadersany et al 2017 disclose a computational method based on a survival CNN to predict the overall survival of patients diagnosed with brain tumors. Pathology image data from tissue biopsies (histology image data) is fed into the model as well as patient-specific genomic biomarkers to predict patient outcomes. This method uses adaptive feedback to simultaneously learn the visual patterns and molecular biomarkers associated with patient outcomes.

Schaumberg et al 2017 takes a different approach. Instead of attempting to mimic the diagnosis of a pathologist to identify tumors, the CNN is trained by watching how long a pathologist has spent looking at each area (referred to as a patch) of a slide under a microscope. The pathology images are of tissue samples of patients with bladder or prostate cancer. The CNN is trained based on a traditional workflow of examining a slide under a microscope. Namely, a pathologist starts by reviewing the slide under a low magnification. When an area with diagnostic value is observed, the pathologist switches to a high magnification objective then, once that review is finished, switches back to low magnification. This process may be repeated several times until a definite diagnosis can be made. Training data is collected by observing a pathologist's motion and observation time over the different areas of the slide, which is used by a CNN to generate a spatial and temporal 'saliency' map of the slide. In this model, a patch can only be classified as 'salient', i.e. potentially cancerous, if the pathologist viewed the patch with a higher magnification objective lens, i.e. switched from a lower magnification to a higher magnification objective lens in order to study a patch more closely. A patch viewed at higher magnification is then classified as 'salient' or 'non-salient' depending on whether the viewing time of the pathologist at this higher magnification is above or below a threshold time. This CNN approach was reported to be able to predict salient slide patches with a test accuracy of 85 to 91%.

Roa-Peña et al 2010 report a study of how different pathologists review virtual slide images with the aim of using the results to improve design of a graphical user interface of a visualization application for presenting virtual slide images to pathologists in low- and high-resolution views. Results suggest that areas of interest are defined by a combination of parameters, namely which areas are visited by the pathologist, the time spent at a visited area and the coincidence level among pathologists, where coincidence level is a measure of correlation between pathologists, i.e. how many of the multiple pathologists that reviewed the same virtual slide visited the same area.

Furthermore, when a test compound, such as a drug candidate, is identified, it is essential to know whether it possesses any adverse health effects. These effects can be subtle and may only be discernible at the microscopic level. To check for adverse health effects, a toxicological pathologist reviews complimentary slide images of tissue samples that have, and have not, been treated with the test compound (Greaves 2012). By comparing the treated and untreated sample slides, a trained pathologist is able to identify changes caused by the test compound from other changes and normal tissue variation. Since the range of normal tissue variation can be quite wide, this is not a straightforward task.

Traditionally, pathologists made their observations on glass slides under a microscope. However, with the introduction of digital scanners it has become possible to create digital images. A digital scanner can acquire an image of an entire glass slide, a so-called whole slide image (WSI), and save it as a digital image data file, a so-called virtual slide, in a largely automated process that does not need a pathologist. The resulting image data file is typically stored in a slide database, from where it is available via a clinical network to a pathologist at a viewing workstation with a high-resolution display, the workstation having a visualization (or viewing) application for this purpose. Digital pathology allows toxicological pathologists to consult with other pathologists to establish diagnosis. Image analysis performed on these digital WISs has reduced or eliminated the need for manual quantification (Dobson et al. 2010). Despite the efficiency improvements introduced by digital pathology, detecting morphological changes due to a test compound remains a tedious and error-prone process that requires a toxicological pathologist to look at many tissue samples and determine whether observed changes are due to the test compound or are due to normal tissue heterogeneity or some other disease process.

A more recent development in digital pathology is that CNN methods have become of research interest. It is becoming increasingly reported that CNN methods are performing as well as, or even better than, pathologists in several areas, such as for identifying and diagnosing tumors from histological images.

Wang et al 2016 describes a CNN approach to detect metastasis of breast cancer to the lymph nodes.

Liu et al 2017 processes image patches extracted from a gigapixel breast cancer histology image with a CNN to detect and localize tumors by assigning a tumor probability to every pixel in the image.

Esteva et al 2017 applies a deep CNN to analyze skin lesions and classify the lesions according to a tree-structured taxonomy into various malignant types, non-malignant types and non-neoplastic types including the malignant types acrolentiginous melanoma, amelanotic melanoma and lentigo melanoma and the non-malignant types blue nevus, halo nevus and Mongolian spot. An image of a skin lesion (for example, melanoma) is sequentially warped into a probability distribution over clinical classes to perform the classification.

Therefore, what are needed are systems and methods that overcomes these significant problems found in the conventional systems as described above.

SUMMARY

According to one aspect of the disclosure, there is provided a method of processing a data set of a histological image, the method comprising:

receiving a data set of a histological image including a two-dimensional array of pixels;

applying a convolutional neural network to generate an output image patch with a two-dimensional array of pixels with a mapping to that of the histology image, the output image patch being generated by assigning one of a plurality of relevance classes to each pixel, wherein the plurality of relevance classes includes at least one class representing a pixel of interest and at least one class representing a pixel that is not of interest, wherein the convolutional neural network has been trained using a training data set comprising histological images and pathologist interaction data, wherein the pathologist interaction data has recorded a plurality of parameters relating to how pathologists have interacted with visualizations of the histological images; and generating a segmentation mask from the output image patch, in which areas of interest occupied by pixels of interest are marked.

With the proposed approach, it is possible to indicate to a pathologist where in the image potential, or potentially significant, tumors, lesions or other clinically relevant features may be located and thus prompt the pathologist to navigate directly to those areas. In this way, the reliability of analysis can be improved, since relevant areas are less likely to be missed by the pathologist. Moreover, the pathologist's throughput can be increased, since the pathologist benefits from being guided to the areas of interest marked by the CNN method and so can be less concerned about accidentally missing relevant areas, and more thorough about reviewing areas that the CNN method has identified as being of interest. The pathologist is also implicitly encouraged to apportion their limited analysis time in a way that takes account of the optional filtering and/or ranking of areas of interest that has been made on the basis of the CNN analysis results, thereby providing a better overall allocation of the pathologist's time in studying a virtual slide image.

The method may further comprise determining a score for each area of interest according to a scoring algorithm which is based on aggregating a score contribution from each pixel of interest contained in the area of interest. In addition, the areas of interest may be ranked according to their score.

Summary statistics may be computed for each area of interest; and applying a filter to the summary statistics of each area of interest to edit the segmentation mask by selecting and deselecting areas of interest according to the filter.

The classes may include multiple classes representing pixels of interest with these classes being associated with increasing levels of interest. In that case, the score contribution may weight pixels according to the level of interest.

The parameters may include one or more of the following in any combination: viewing time of a pixel; viewing magnification of a pixel; pixels at locations or areas on the histological images associated with pathologists' annotations; and pixels at locations or areas on the histological images that were subject to a user command to view at higher magnification.

In the training data set, the pathologist interaction data for a given histological image may include interactions from multiple pathologists, and the parameters include a correlation factor between interaction with the same histological image from multiple pathologists.

The convolutional neural network is applied in certain embodiments by: extracting image patches from the histological image, the image patches being area portions of the histological image or set thereof having a size defined by numbers of pixels in width and height; providing the convolutional neural network with a set of weights and a plurality of channels, each channel corresponding to one of the plurality of relevance classes to be identified; inputting each image patch as an input image patch into the convolutional neural network; performing multi-stage convolution to generate convolution layers of ever decreasing dimensions up to and including a final convolution layer of minimum dimensions, followed by multi-stage transpose convolution to reverse the convolutions by generating deconvolution layers of ever increasing dimensions until a layer is recovered matched in size to the input image patch, each pixel in the recovered layer containing a probability of belonging to each of the relevance classes; and assigning the relevance class to each pixel of the recovered layer based on said probabilities to arrive at an output image patch.

Moreover, the output image patches may be assembled into a probability map for the histological image. Further, the areas of interest in the histological image may be defined according to the probability map.

In our current implementation, in each successive convolution stage, as the dimensions decrease, the depth increases, so that the convolution layers are of ever increasing depth as well as ever decreasing dimensions, and in each successive transpose convolution stage, as the dimensions increase, the depth decreases, so that the deconvolution layers are of ever decreasing depth as well as ever increasing dimensions. The final convolution layer then has a maximum depth as well as minimum dimensions. Instead of the approach of successive depth increases and decreases through respectively the convolution and deconvolution stages, an alternative would be to design a neural network in which every layer except the input layer and the output layer has the same depth.

In certain embodiments, the convolutional neural network has one or more skip connections. Each skip connection takes intermediate results from at least one of the convolution layers of larger dimensions than the final convolution layer and subjects those results to as many transpose convolutions as needed, which may be none, one or more than one, to obtain at least one further recovered layer matched in size to the input image patch. These are then combined with the above-mentioned recovered layer prior to said step of assigning a class to each pixel. A further processing step combines the recovered layer with each of the further recovered layers in order to recompute the probabilities, thereby taking account of the results obtained from the skip connections.

In certain embodiments, a softmax operation is used to generate the probabilities.

The image patches extracted from the histological image(s) may cover the whole area of the image(s). The patches may be non-overlapping image tiles or image tiles that overlap at their margins to aid stitching of the probability map. While each image patch should have a fixed number of pixels in width and height to be matched to the CNN, since the CNN will be designed to accept only a fixed size of pixel array, this does not mean that each image patch must correspond to the same physical area on the histological image, because pixels in the histological image may be combined into a lower resolution patch covering a larger area, e.g. each 2×2 array of neighboring pixels may be combined into one 'super'-pixel to form a patch with four times the physical area of a patch extracted at the native resolution of the histological image.

The method can be performed for prediction once the CNN has been trained. The purpose of the training is to assign suitable weight values for the inter-layer connections. For training, the records that are used will include ground truth data which assigns each pixel in the histological image or set thereof to one of the classes. The ground truth data will be based on use of an expert clinician to annotate a sufficiently large number of images. Training is carried out by iteratively applying the CNN, where each iteration involves adjusting the weight values based on comparing the ground truth data with the output image patches. In our current implementation, the weights are adjusted during training by gradient descent.

The histological image data set may include only one histological image or may be a composite of a plurality of histological images, such as for example obtained from differently stained, adjacent sections of a region of tissue. In some embodiments the CNN is applied to one histological image at a time (which may be a composite). In other embodiments, the CNN may be applied in parallel to each of the images of a set of images taken from differently stained, adjacent sections of a region of tissue.

The results may be displayed on a display to a clinician. Namely, a histological image can be displayed with its associated probability map, e.g. overlaid thereon or alongside each other. The scores may also be displayed in some convenient manner, e.g. with text labels on or pointing to the areas of interest, or alongside the image.

The results from the above method may be presented to a user with the aid of a visualization application for generating a visualization for the histological image dependent on the segmentation mask. The visualization may be generated having regard to the ranking so as to include a visual indication of the ranking.

There are various options for the layout of the graphical user interface. The visualization, that is suitable for display on a display apparatus, may include an overview viewing pane and a segmentation mask viewing pane. The overview viewing pane and the segmentation mask viewing pane may be displayed with the segmentation mask overlaid on, or alongside, the histological image. The visualization may also be in the form of a montage comprising a plurality of juxtaposed images for all or selected ones of the areas of interest. The visualization application may include a graphical user interface selection control operable to permit a user to interact with the visualization so as to select an area of interest.

An agent of the visualization application may be provided which monitors a user's interaction with visualizations of the histological image data set in order to track which of the areas of interest the user has specifically viewed. Based on the tracking, the visualization application may incorporate a checking function which is called responsive to a user command to end a visualization session on a histological image, where the checking function performs a check of whether the user has specifically viewed a logical sample of the areas of interest, where this check may be limited by ranking in some way. For example, it may only check that the top-ranked areas of interest have been specifically viewed, e.g. the top 5 or 10, or it may only check that the list of areas of interest specifically viewed includes at least the top ranked area of interest and all other areas of interest in the ranking down to the lowest ranked area of interest that was specifically viewed by the user. For example, if the user has specifically viewed only the third and fifth ranked area of interest, the checking function may prompt the user to specifically view also the first, second and fourth ranked areas of interest. When the check indicates the user has not specifically viewed a logical sample of the areas of interest, a notification may be issued to the user which requires a further confirmation input prior to ending the visualization session and/or the user may be guided to view that or those areas of interest that have not yet been specifically viewed.

The results from the above method may be used to assist data compression of the histological image data. In particular, variable image compression may be applied to the histological image data set which takes account of the areas of interest found by the convolutional neural network. Namely, a compression algorithm may be applied which preferentially compresses pixels outside the areas of interest, thereby to generate a compressed version of the histological image data set which may then be stored separately from or with the data set from which it was derived, or by overwriting the source data set.

The compression algorithm may be lossless or lossy. The compression standard being used may be lossless only or lossy only or may combine lossless and lossy compression options.

The above method of identifying areas of interest may be integrated in a workflow that includes acquiring the histological image data set. Namely, the method may include image data acquisition based on providing a slide containing a histological sample; and using a slide scanner to scan the slide and obtain a histological image data set. The above method of identifying areas of interest with a CNN may then be applied. The results may then be stored either with the histological image data set, where the histological image data set may be as acquired, or a compressed version using the variable compression algorithm described above.

The CNN processing may be integrated with the slide scanner, and be performed by the slide scanner or its control computer, for example before storing the acquired histological image data as a record into a virtual slide library or other data repository via a suitable network connection. Another option is to integrate the CNN processing with the data repository, so the acquired histological image data is first transferred from the slide scanner to the data repository before the CNN processing is applied.

A further aspect of the disclosure relates to a method of operating a visualization application for histological images. The method comprises providing a computer apparatus loaded with a visualization application operable to interactively display histological images of histological image data sets to a user. The computer apparatus loads a histological image data set, for example over a network connection from a data repository, where the histological image data set is one that has been pre-processed according to the above CNN method and so includes a segmentation mask that marks areas of interest in the histological image. The loading preferentially loads small-area sub-images of the histological image data set that contain the areas of interest before loading other sub-images that do not contain any areas of interest. In this way, if there is a lag in the data transfer from where the image data is stored to the computer apparatus, e.g. by bandwidth limitation of a network connection, then the high-resolution image data relating to the areas of interest is loaded first. The small-area sub-images may be loaded at native resolution as stored in the histological image data set. When the histological image data set has been pre-processed to rank the areas of interest, the small-area sub-images can be loaded having regard to ranking order.

Further aspects of the disclosure relate to computer program products bearing machine readable instructions for performing any of the above methods.

According to a further aspect of the disclosure, there is provided a computer apparatus for identifying areas of interest in a histological image, the apparatus comprising: an input operable to receive a histological image data set from a record stored in a memory; and a CNN processing module configured to perform the above CNN methods. The computer apparatus may be provided with an output operable to store metadata relating to the segmentation mask into a record that also contains the histological image data set, so that the metadata is linked to the histological image data set. A display may be connected to the computer apparatus via a display output which is operable to transmit the histological image data set and the segmentation mask to the display such that the histological image can be displayed having regard to the segmentation mask.

According to a further aspect of the disclosure, there is provided a system, e.g. a clinical network, comprising: a computer apparatus as specified above in combination with one or more of the following elements. One system element is a data repository configured to store records of patient data including histological images. It will be understood that suitable network connections will enable transfer of patient data records or parts thereof between the computer apparatus and the data repository. Another system element is an image acquisition apparatus operable to acquire histological images. The image acquisition apparatus may be operable to store acquired histological images to records in the data repository via a suitable network connection.

According to a further aspect of the disclosure, there is provided a slide scanner for acquiring histological image data sets from histology slides, the slide scanner comprising: a microscope module including a slide loader and objective lens; a control computer operable to control the microscope module to acquire a histological image data set; and a neural network processing module operable to perform the above CNN processing methods to identify the areas of interest. The slide scanner may further comprise a compression module operable to perform the above-specified variable compression of the histological image data set based on the areas of interest.

According to a further aspect of the disclosure, there is provided a computer apparatus loaded with a visualization application for interactively displaying histological images of histological image data sets to a user, the computer apparatus comprising: memory composed of a plurality of memory tiers arranged in a hierarchy of increasing latency, wherein at least the lowest latency memory tier is a cache tier; and a visualization application. The visualization application is operable to access a histological image data set stored in a higher latency part of the memory, wherein the histological image data set has been pre-processed according to any of the above CNN methods, and so includes a segmentation mask that marks areas of interest in the histological image, wherein the histological image data set is larger than can be retained solely in the lowest latency memory tier. Moreover, the visualization application is responsive to receiving a command to view the histological image data set by preferentially pre-loading into, and retaining in, the at least one cache tier higher resolution small-area sub-images of the data set containing the areas of interest, compared to other sub-images that do not contain any areas of interest. When the histological image data sets have been pre-processed to rank the areas of interest, the small-area sub-images are preferentially loaded into, and retained in, the at least one cache tier having regard to ranking order, so that high ranking maps to low latency and/or preferential cache retention.

It will be understood that in at least some embodiments the histological image(s) are digital representations of a two-dimensional image taken of a sectioned tissue sample by a microscope, in particular a light microscope, which may be a conventional optical microscope, a confocal microscope or any other kind of microscope suitable for obtaining histological images of unstained or stained tissue samples. In the case of a set of histological images, these may be of a succession of microscope images taken of adjacent sections (i.e. slices) of a region of tissue, wherein each section may be differently stained.

In summary of one aspect of the disclosure, a convolutional neural network is applied to a histological image to identify areas of interest. The CNN classifies pixels according to relevance classes including one or more classes indicating levels of interest and at least one class indicating lack of interest. The CNN is trained on a training data set including data which has recorded how pathologists have interacted with visualizations of histological images. In the trained CNN, the interest-based pixel classification is used to generate a segmentation mask that defines areas of interest. The mask can be used for different purposes. It can be used by a visualization application to indicate where in an image clinically relevant features may be located. Further, it can be used to guide variable data compression of the histological image. Moreover, it can be used to control loading of image data in either a client-server model or within a memory cache policy.

In accordance with another aspect of the disclosure a neural network can be used to identify potentially hazardous changes in tissue caused by a test compound resulting in faster, more reliable and less expensive toxicology studies. As a neural network we propose the use of an autoencoder (Elman and Zipser 1988). The autoencoder can be trained in a self-supervised learning process with a training data set including tissue samples of a certain tissue type that are untreated and/or treated with a compound, other than the test compound, which is known to be non-toxic. Through the training process, the autoencoder learns which variations in the pathology images of the tissue type are within normal bounds, bearing in mind for some tissue types the amount of heterogeneity is large. The trained autoencoder can then be applied to detect and rank tissue areas in order of their deviation from the normal variation seen in a particular tissue type. By examining the areas identified by the autoencoder, i.e. the areas determined by the autoencoder as lying outside the normal range of heterogeneity for the tissue type, a toxicological pathologist can determine if adverse health effects are present more quickly and more reliably. The proposed approach is able to reduce the likelihood that adverse health effects of a test compound are missed and to increase the speed of the toxicological pathologist workflow.

According to one aspect of the disclosure a computer-automated method is provided for processing a histological image of a tissue sample of a given tissue type that has been treated with a test compound. The method comprises: receiving a histological image of a tissue sample that has been treated with a test compound, the histological image comprising a two-dimensional array of pixels, which can be subdivided into a plurality of image tiles; providing an autoencoder that has been trained with a training data set comprising a plurality of histological images of tissue samples of said given tissue type that have not been treated with the test compound; applying the autoencoder to the histological image to generate a toxicity map for the histological image. The autoencoder is operated on a tile-by-tile basis to extract an image tile from the histological image; input the image tile to the autoencoder; receive a corresponding image tile as output; and compute a distance between the input and output image tiles. It is these distances that are used to generate the toxicity map. The toxicity map can then be saved, e.g. as metadata linked to the histological image as may be contained in a record. The record may be one of a plurality of such records collectively stored in a data repository. The data repository may be a database, such as a virtual slide library, or a simple file structure such as a folder of a storage drive.

In some embodiments, the distance for each tile is compared to a threshold value and that image tile is labeled as toxic if the distance exceeds the threshold value. These binary tile results can be used to generate the toxicity map as a binary mask based on whether each tile is labeled as toxic or not. The toxicity map may also be in the form of a heat map in which tiles labeled as toxic are assigned a temperature value proportional to their distance value. The values may be filtered such that the heat map assigns a common base temperature value to non-toxic tiles, i.e. tiles not labeled as toxic, so that in a visualization non-toxic tiles are uniformly visualized, e.g. by not being marked at all, or by being marked in some way that positively identifies them to the user as being non-toxic, e.g. by a translucent wash.

For a histological image as a whole a single binary label of toxic or not toxic can be generated by aggregating the tile results. Namely, an overall toxicity label can be generated, which is a binary label designating a histological image as toxic if any one of its image tiles has been determined to be toxic. The overall toxicity label is thus only non-toxic when none of its image tiles has been determined to be toxic.

As an extension of the above method, a segmentation algorithm may be applied to the toxicity map to group toxic tiles into toxic areas and thereby generate a segmentation mask of the toxic areas. The segmentation mask can also be saved to the toxicity map.

The toxicity map of a given histological image may be a collection of two or more maps (e.g. binary, heat, segmented), or just one map.

The method may also rank the toxic tiles, or toxic areas, according to toxicity as measured by the distances, and this ranking may be stored into the toxicity map.

The results of the histological image processing, namely the toxicity map, can be usefully combined with a visualization application that is configured to create visualizations of the histological images having regard to their toxicity maps.

There are various visualization options. The visualization may include an overview viewing pane in which the toxicity map is overlaid on the histological image. The overview viewing pane may include a ranking label for each toxic area. The visualization may include respective overview viewing panes in which the toxicity map and the histological image are presented adjacent each other for one-to-one comparison. The visualization application may include a user interface control for selecting one or more of the toxic areas. A selected toxic area may then have its summary statistics displayed in a pop-up window or side-bar, or permit further numerical processing to be initiated by the user on the selected toxic area. The visualization may include a close-up viewing pane which presents a visualization of whichever toxic area is currently selected, where the close-up viewing pane shows a high-resolution, zoomed in view of the currently selected toxic area. The toxic area selection control may have a scroll function for sweeping through the toxic areas in order of ranking, e.g. using a scroll wheel of a mouse.

Another form of visualization is to present the toxic areas in a list ordered by their ranking, with each toxic area being presented as a thumbnail image. This may be done in combination with the above-mentioned close-up viewing pane in a split screen format, where the close-up viewing pane initially shows the highest ranked toxic area at high resolution, and then changes to show whichever list item is currently selected by the user.

A further form of visualization is to present the toxic areas in a mosaic of images arranged to fit onto the display. Each mosaic element may have a ranking label shown.

The threshold value used for setting the binary mask can be set by and/or adjusted by a user, for example with a suitable user control in the visualization application.

In visualizations of the heat map, it may be presented in various ways, for example with a color scale or gray scale, or with contour lines.

For training the autoencoder, it may be helpful if the extracted image tiles used for training are of the same size as those which are to be subsequently used in the live system. That is the training tiles are the same size as the tiles of the live system for generating the toxicity map that are extracted from the histological image of the tissue sample that has been treated with the test compound.

A further aspect of the disclosure relates to a computer program product bearing machine readable instructions for performing the above methods.

A still further aspect of the disclosure relates to a computer apparatus for processing a histological image of a tissue sample of a given tissue type that has been treated with a test compound, the apparatus comprising: an input operable to receive a histological image of a tissue sample that has been treated with a test compound, the histological image comprising a two-dimensional array of pixels, which can be subdivided into a plurality of image tiles; a processing module loaded with machine-readable instructions for executing an autoencoder that has been trained with a training data set comprising a plurality of histological images of tissue samples of said given tissue type that have not been treated with the test compound, the processing module being configured to: apply the autoencoder to the histological image on a tile-by-tile basis to: extract an image tile from the histological image; input the image tile to the autoencoder; receive a corresponding image tile as output; and compute a distance between the input and output image tiles; and generate a toxicity map for the histological image based on the computed distances; and an output operable to save the toxicity map.

The apparatus may further comprise: a visualization application operable to create visualizations of histological images having regard to their toxicity maps. A display may also be provided to receive and present visualizations from the visualization application.

Further aspects of the disclosure provide a system comprising the above-specified computer apparatus in combination with one or more elements. In particular, the system may include an image acquisition apparatus operable to acquire histological images, such as a digital slide scanner. The system may also include a data repository, such as a virtual slide library, configured to store records of patient data including histological images with associated toxicity maps. It will be understood that network connections enabling transfer of patient data records or parts thereof between the computer apparatus and the data repository may also be part of the system.

In summary of this aspect of the disclosure, a method, apparatus and system are provided for processing a histological image of a tissue sample of a given tissue type that has been treated with a test compound in order to detect toxic reactions to the test compound. An autoencoder is used that has been trained with a training data set comprising histological images of tissue samples which are of the given tissue type, but which have not been treated with the test compound. The trained autoencoder is applied to detect and optionally also rank tissue areas in order of their deviation from the normal variation seen in the tissue type, and so build up a toxicity map of the image. The toxicity map can then be used to direct a toxicological pathologist to examine the areas identified by the autoencoder as lying outside the normal range of heterogeneity for the tissue type. This support for the pathologist will on average make the pathologist's review quicker and also more reliable.

It will be understood that in at least some embodiments the histological image(s) are digital representations of a two-dimensional image taken of a sectioned tissue sample by a microscope, in particular a light microscope, which may be a conventional optical microscope, a confocal microscope or any other kind of microscope suitable for obtaining histological images of unstained or stained tissue samples. In the case of a set of histological images, these may be of a succession of microscope images taken of adjacent sections (i.e. slices) of a region of tissue, wherein each section may be differently stained.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1A:
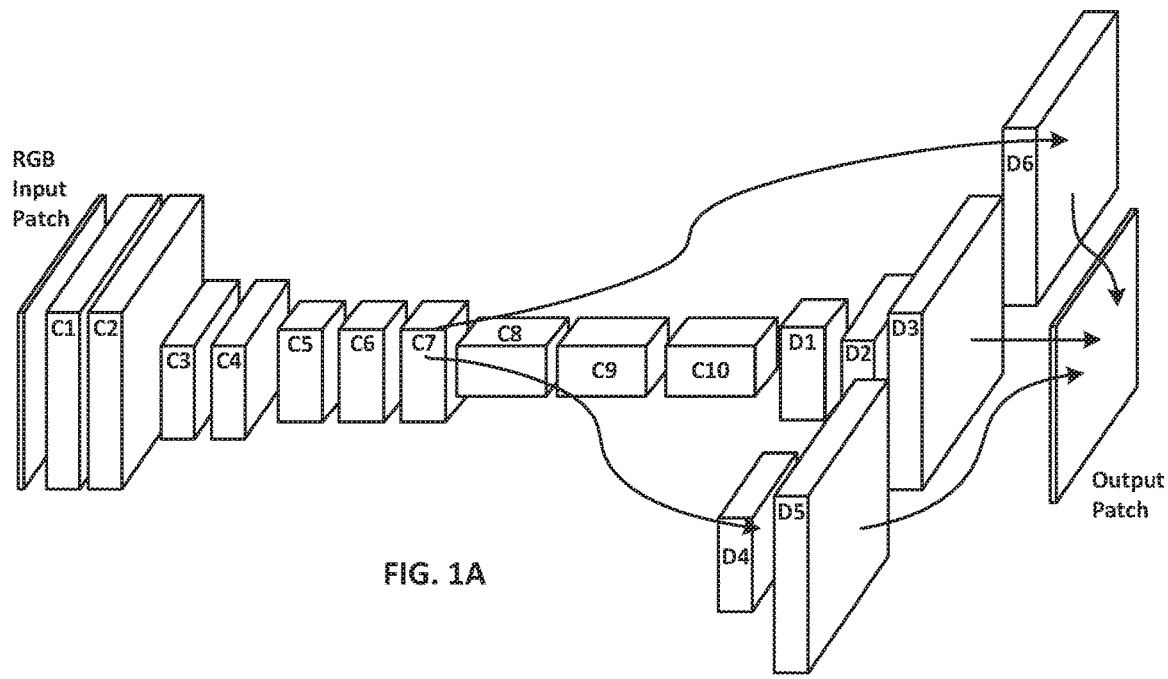
FIG. 1A is a schematic drawing of a neural network architecture used in one embodiment of the invention.

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

In short summary, we describe a computer-automated method which detects areas of clinical interest automatically based on identifying areas which an experienced pathologist would be expected to review closely. The method is based on applying a convolutional neural network which has been trained using a training data set comprising histological images and data relating to how pathologists have interacted with those images in the course of diagnostic review using a visualization application. The interaction is measured by logging selected parameters that are indicative of how the pathologist has interacted with a visualization of a histological image. The CNN generates an output image patch with a two-dimensional array of pixels with a mapping to that of the histology image, the output image patch being generated by assigning one of a plurality of relevance classes to each pixel, wherein the plurality of relevance classes includes one or more classes representing a pixel of interest and one or more classes representing a pixel that is not of interest. Segmentation is then applied to group the pixels into areas of interest according to their classification. When there are two or more classes representing pixels of interest, then these classes may be associated with increasing levels of interest, or be associated with different types of interest. In the latter case, when the training data is compiled it will be necessary to know what the interest of the reviewing pathologist was, which may be inferred from the nature of the user's interaction, or may be an a priori manual input by the pathologist, e.g. to indicate that he or she is screening for a particular type of cancer.

The method is applied to a single input image, such as a WSI, or a set of input images, such as a set of WSIs. Each input image is a digitized, histological image, such as a WSI. In the case of a set of input images, these may be differently stained images of adjacent tissue sections. We use the term stain broadly to include staining with biomarkers as well as staining with conventional contrast-enhancing stains. The histological image data set may thus be a single WSI obtained from a single scan, or a composite made up of a plurality of histological image data sub-sets, each sub-set relating to a differently stained, adjacent section of a region of tissue. Another composite example is when there are a plurality of histological image data sub-sets, each sub-set relating to a different depth of focus in the same sample, i.e. a so-called z-stack.

The proposed computer-automated method for finding areas of interest uses a convolutional neural network (CNN) to classify each pixel into a relevance class representing whether the pixel is of interest or is not of interest.

The neural network in our implementation is similar in design to the VGG-16 architecture available at: <http://www.robots.ox.ac.uk/~vgg/research/very_deep/> and described in Simonyan and Zisserman 2014, the full contents of which are incorporated herein by reference.

The input image is a pathology image, for example one stained with any one of several conventional stains as discussed in more detail elsewhere in this document. For the CNN, image patches are extracted of certain pixel dimensions, e.g. 128×128, 256×256, 512×512 or 1024×1024 pixels. It will be understood that the image patches can be of arbitrary size and need not be square, but that the number of pixels in the rows and columns of a patch conform to $2n$, where n is a positive integer, since such numbers will generally be more amenable for direct digital processing by a suitable single CPU (central processing unit), GPU (graphics processing unit) or TPU (tensor processing unit), or arrays thereof.

We note that 'patch' is a term of art used to refer to an image portion taken from a WSI, typically with a square or rectangular shape. In this respect we note that a WSI may contain a billion or more pixels (gigapixel image), so image processing will typically be applied to patches which are of a manageable size (e.g. ca. 500×500 pixels) for processing by a CNN. The WSI will thus be processed on the basis of splitting it into patches, analyzing the patches with the CNN, then reassembling the output (image) patches into a probability map of the same size as the WSI. The probability map can then be overlaid, e.g. semi-transparently, on the WSI, or part thereof, so that both the pathology image and the probability map can be viewed together. In that sense the probability map is used as an overlay image on the pathology image. The patches analyzed by the CNN may be of all the same magnification, or may have a mixture of different magnifications, e.g. 5×, 20×, 50× etc. and so correspond to different sized physical areas of the sample tissue. By different magnifications, these may correspond to the physical magnifications with which the WSI was acquired, or effective magnifications obtained from digitally downscaling a higher magnification (i.e. higher resolution) physical image.

FIG. 1A is a schematic drawing of our neural network architecture. Layers C1, C2 . . . C10 are convolutional layers. Layers D1, D2, D3, D4, D5 and D6 are transpose convolution (i.e. deconvolutional) layers. The lines interconnecting certain layers indicate skip connections between convolutional, C, layers and deconvolutional, D, layers. The skip connections allow local features from larger dimension, shallower depth layers (where "larger" and "shallow" mean a convolutional layer of lower index) to be combined with the global features from the last (i.e. smallest, deepest) convolutional layer. These skip connections provide for more accurate outlines. Maxpool layers, each of which is used to reduce the width and height of the patch by a factor of 2, are present after layers C2, C4 and C7, but are not directly shown in the schematic, although they are shown by implication through the consequential reducing size of the patch. In some implementations of our neural network the maxpool layers are replaced with 1×1 convolutions resulting in a fully convolutional network.

The convolutional part of the neural network has the following layers in sequence: input layer (RGB input image patch); two convolutional layers, C1, C2; a first maxpool layer (not shown); two convolutional layers C3, C4; a second maxpool layer (not shown); three convolutional layers, C5, C6, C7, and a third maxpool layer (not shown). The output from the second and third maxpool layers is connected directly to deconvolutional layers using skip connections in addition to the normal connections to layers C5 and C8 respectively.

The final convolutional layer, C10, the output from the second maxpool layer (i.e. the one after layer C4) and the output from the third maxpool layer (i.e. the one after layer C7), are then each connected to separate sequences of "deconvolution layers" which upscale them back to the same size as the input (image) patch, i.e. convert the convolutional feature map to a feature map which has the same width and height as the input image patch and a number of channels (i.e. number of feature maps) equal to the number of relevance classes to be detected, for example one class for pixels of interest and one class for pixels that are not of interest. For the second maxpool layer, we see a direct link to the layer D6 since only one stage of deconvolution is needed. For the third maxpool layer, two stages of deconvolution are needed, via intermediate deconvolution layer D4, to reach layer D5. For the deepest convolutional layer C10, three stages of deconvolution are needed, via D1 and D2 to layer D3. The result is three arrays D3, D5, D6 of equal size to the input patch.

A simplified, albeit probably less-well performing, version of what is illustrated in FIG. 1 could omit the skip connections, in which case layers D4, D5 and D6 would not be present and the output patch would be computed solely from layer D3.

Figure 1B:
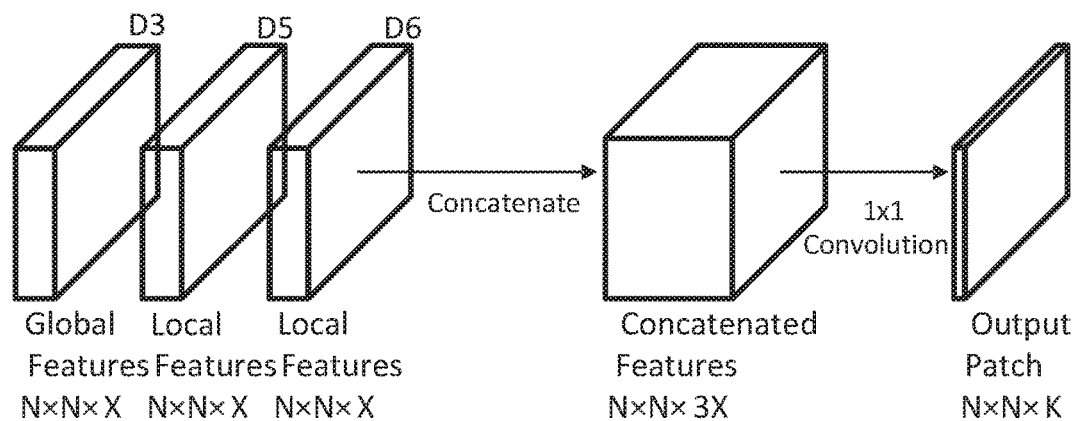
FIG. 1B shows how within the neural network architecture of FIG. 1A, global and local feature maps are combined to generate a feature map that predicts an individual class for each pixel in an input image patch according to an embodiment.

FIG. 1B shows in more detail how the final steps in the neural network architecture of FIG. 1A are carried out. Namely, global feature map layer D3 and local feature map layers D5, D6 are combined to generate a feature map that predicts an individual class for each pixel of the input image patch. Specifically, FIG. 2 shows how the final three transpose convolution layers D3, D5, D6 are processed to the relevance class output patch.

We now discuss how the above-described approach differs from a known CNN used currently in digital pathology. This known CNN assigns one class selected from multiple available classes to each image patch. Examples of such type of CNN are in the papers by Wang et al 2016, Liu et al 2017, Cruz-Roa et al 2017 and Vandenberghe et al 2017. However, what we have just described is that, within a given image patch, one class selected from multiple available classes is assigned to each and every pixel. Therefore, instead of generating a single class label for each image patch, our neural network outputs a class label for each individual pixel of a given patch. Our output patch has a one-to-one pixel-to-pixel correspondence with the input patch such that each pixel in the output patch has assigned to it one of the multiple available classes (e.g. not-of-interest & of-interest in a binary classification).

In such known CNNs, to assign a single class to each patch, a series of convolutional layers is employed followed by one or several fully connected layers, followed by an output vector which has as many values as there are classes to detect. The predicted class is determined by the location of the maximum value in the output vector.

A trained CNN will take, as input, pixels from a digital slide image and return a vector of probabilities for each pixel. The vector is of length N where N is the number of classes the CNN has been trained to detect. For example, if a CNN has been trained to distinguish between three classes, of-interest, not-of-interest tissue and not-of-interest non-tissue, the vector v will be of length 3. Each coordinate in the vector indicates the probability that the pixel belongs to a specific class. So v[0] may indicate the probability that the pixel belongs to the single class for areas of interest, v[1] the probability the pixel belongs to the not-of-interest class for tissue and v[2] the probability it belongs to the not-of-interest class for pixels that are not tissue. The class of each pixel is determined from the probability vector. A simple method of assigning a pixel to a class is to assign it to the class for which it has the highest probability.

To predict the class of individual pixels, our CNN uses a different architecture following the convolutional layers. Instead of a series of fully connected layers, we follow the convolutional layers with a series of transpose convolutional layers. The fully connected layers are removed from this architecture. Each transpose layer doubles the width and height of the feature maps while at the same time halving the number of channels. In this manner, the feature maps are upscaled back to the size of the input patch.

In addition, to improve the prediction, we use skip connections as described in Long et al 2015, the full contents of which is incorporated herein by reference.

The skip connections use shallower features to improve the coarse predictions made by upscaling from the final convolutional layer C10. The local features from the skip connections contained in layers D5 and D6 of FIG. 1A are concatenated with the features generated by upscaling the global features contained in layer D3 of FIG. 1 from the final convolutional layer. The global and local feature layers D3, D5 and D6 are then concatenated into a combined layer as shown in FIG. 1B.

From the concatenated layer of FIG. 1B (or alternatively directly from the final deconvolutional layer D3 in the case that skip connections are not used), the number of channels is reduced to match the number of classes by a 1×1 convolution of the combined layer. A softmax operation on this classification layer then converts the values in the combined layer into probabilities. The output patch layer has size N×N×K, where N is the width and height in pixels of the input patches and K is the number of classes that are being detected. Therefore, for any pixel P in the image patch there is an output vector V of size K. A unique class can then be assigned to each pixel P by the location of the maximum value in its corresponding vector V.

The CNN thus labels each pixel as of-interest or not-of-interest.

Our specific neural network implementation is configured to operate on input images having certain fixed pixel dimensions. Therefore, as a preprocessing step, both for training and prediction, patches are extracted from the WSI which have the desired pixel dimensions, e.g. N×N×n pixels, where n=3 in the case that each physical location has three pixels associated with three primary colors—typically RGB, when the WSI is a color image acquired by a conventional visible light microscope. (As mentioned further below 'n' may be 3 times the number of composited WSIs in the case the two or more color WSIs are combined.) Moreover 'n' would have a value of one in the case of a single monochrome WSI. To make training faster the input patches are also centered and normalized at this stage.

Our preferred approach is to process the entire WSI, or at least the entire area of the WSI which contains tissue, so the patches in our case are tiles that cover at least the entire tissue area of the WSI. The tiles may be abutting without overlap, or have overlapping edge margin regions of for example 1, 2, 3, 4, 5, 6, 7, 8, 9 or 10 pixels wide so that the output patches of the CNN can be stitched together taking account of any discrepancies. Our approach can however, if desired, also be applied to a random sample of patches over the WSI which are of the same or different magnification, as in the prior art, or as might be carried out by a pathologist.

Our neural network is similar in design to the VGG-16 architecture of Simonyan and Zisserman 2014. It uses very small 3×3 kernels in all convolutional filters. Max pooling is performed with a small 2×2 window and stride of 2. In contrast to the VGG-16 architecture, which has a series of fully connected layers after the convolutional layers, we follow the convolution layers with a sequence of "deconvolutions" (more accurately transpose convolutions) to generate segmentation masks. This type of upsampling for semantic segmentation has previously been used for natural image processing by Long et al 2015, the full contents of which are incorporated herein by reference.

Each deconvolutional layer enlarges the input feature map by a factor of two in the width and height dimensions. This counteracts the shrinking effect of the maxpool layers and results in class feature maps of the same size as the input images. The output from each convolution and deconvolutional layer is transformed by a non-linear activation layer. At present, the non-linear activation layers use the rectifier function ReLU (x)=max (0, x)ReLU(x)=max(0,x). Different activation functions may be used, such as ReLU, leaky ReLU, eLU, etc. as desired.

The proposed method can be applied without modification to any desired number of relevance classes. The constraint is merely the availability of suitable training data which has been classified in the manner that it is desired to replicate in the neural network. For example, if the training data distinguishes between the discipline or sub-discipline of the reviewing clinical expert, then there can be a different relevance class for each discipline or sub-discipline. Another example would be different relevance classes for different disease types, so each relevance class could be specific to a certain tumor type, for example. In that case the training data would need to know what disease type the reviewer was tasked with looking for in the pathology images. It may also be helpful for there to be multiple classes for not of interest. For example, it may be possible to distinguish between areas on a WSI that do not contain tissue at all, and so are fundamentally not of any interest, and those which contain tissue, but not any tissue that is of clinical interest. The training data is likely to reflect this distinction, since the pathologist will usually skip over non-tissue areas completely, but review all or at least most tissue areas at low magnification.

A softmax regression layer (i.e. multinomial logistic regression layer) is applied to each of the channel patches to convert the values in the feature map to probabilities.

After this final transformation by the softmax regression, a value at location (x, y) in a channel C in the final feature map contains the probability, P(x, y), that the pixel at location (x, y) in the input image patch belongs to the type detected by channel C.

It will be appreciated that the number of convolution and deconvolution layers can be increased or decreased as desired and subject memory limitations of the hardware running the neural network.

We train the neural network using mini-batch gradient descent. The learning rate is decreased from an initial rate of 0.1 using exponential decay. We prevent neural network overfitting by using the "dropout" procedure described by Srivastava et al 2014, the full contents of which are incorporated herein by reference. Training the network may be done on a GPU, CPU or a FPGA using any one of several available deep learning frameworks. For our current implementation, we are using Google Tensorflow, but the same neural network could have been implemented in another deep learning framework such as Microsoft CNTK.

The neural network outputs probability maps of size N×N×K, where N is the width and height in pixels of the input patches and K is the number of classes that are being detected. These output patches are stitched back together into a probability map of size W×H×K, where W and H are the width and height of the original WSI before being split into patches.

The probability maps can then be collapsed to a W×H label image by recording the class index with maximum probability at each location (x, y) in the label image.

In its current implementation, our neural network assigns every pixel to one of two classes: of-interest and not-of-interest.

When multiple relevance classes are used for areas of interest, the output image can be post-processed into a simpler binary classification with a single class for areas of interest and a single class for areas not of interest, e.g. different relevance classes for of-interest areas can be combined. The binary classification may be used as an option when creating images from the base data, while the multi-class of-interest classification (or not-of-interest classification) is retained in the saved data.

While the above description of a particular implementation for our invention has concentrated on a specific approach using a CNN, it will be understood that our approach can be implemented in a wide variety of different types of convolutional neural network. In general, any neural network that uses convolution to detect increasingly complex features and subsequently uses transpose convolutions ("deconvolutions") to upscale the feature maps back to the width and height of the input image should be suitable.

Figure 1C:
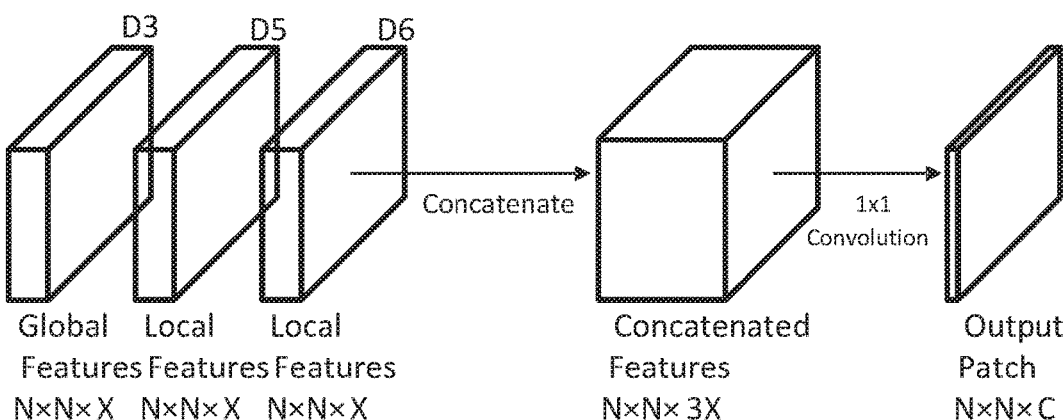
FIG. 1C shows how within the neural network architecture of FIG. 1A global and local feature maps are combined to generate a feature map that predicts an individual class for each pixel in an input image patch according to an embodiment.

FIG. 1C shows in more detail how the final steps in the neural network architecture of FIG. 1A are carried out according to an embodiment. Namely, global feature map layer D3 and local feature map layers D5, D6 are combined to generate a feature map that predicts an individual class for each pixel of the input image patch. Specifically, FIG. 1B shows how the final three transpose convolution layers D3, D5, D6 are processed to the output patch.

Our neural network outputs an image that resembles the input image as closely as possible. The quality of the reconstruction will depend on how closely the input image resembles images in the training set. For an image type that has been seen often during training the reconstructed image will be a close match to the input image. For an image type not present in the training set, such as an image showing toxic effects, the resemblance between the input image and the reconstructed image will be lowered.

A trained autoencoder CNN will take, as input, pixels from a digital slide image and return a set of pixels that attempt to match the input pixels as closely as possible. To prevent the network from simply learning to copy the input pixels to the output a sparsity constraint is added to the loss function during training. The sparsity constraint increases the loss when too many activations are firing at the same time. This forces the network to learn encodings that require only a small number of units to be active for any given input.

To improve the quality of the reconstructed image, our autoencoder CNN uses a different architecture following the convolutional layers. Instead of a series of fully connected layers, we follow the convolutional layers with a series of transpose convolutional layers. The fully connected layers are removed from this architecture. Each transpose layer doubles the width and height of the feature maps while at the same time halving the number of channels. In this manner, the feature maps are upscaled back to the size of the input patch.

In addition, to improve the prediction, we use skip connections as described in Long et al 2015, the full contents of which is incorporated herein by reference. The skip connections use shallower features to improve the coarse predictions made by upscaling from the final convolutional layer C10. The local features from the skip connections contained in layers D5 and D6 of FIG. 1A are concatenated with the features generated by upscaling the global features contained in layer D3 of FIG. 1A from the final convolutional layer. The global and local feature layers D3, D5 and D6 are then concatenated into a combined layer as shown in FIG. 1C.

From the concatenated layer of FIG. 1C (or alternatively directly from the final deconvolutional layer D3 in the case that skip connections are not used), the number of channels is reduced to match the number of channels of the input image by a 1×1 convolution of the combined layer. The output patch layer has size N×N×C, where N is the width and height in pixels of the input patches and C is the number of channels in the input image.

Our specific neural network implementation is configured to operate on input images having certain fixed pixel dimensions. Therefore, as a preprocessing step, both for training and prediction, patches are extracted from the WSI which have the desired pixel dimensions, e.g. N×N×n pixels, where n=3 in the case that each physical location has three pixels associated with three primary colors—typically RGB, when the WSI is a color image acquired by a conventional visible light microscope. (As mentioned further below 'n' may be 3 times the number of composited WSIs in the case the two or more color WSIs are combined.) Moreover 'n' would have a value of one in the case of a single monochrome WSI. To make training faster the input patches are also centered and normalized at this stage.

Our preferred approach is to process the entire WSI, or at least the entire area of the WSI which contains tissue, so the patches in our case are tiles that cover at least the entire tissue area of the WSI. The tiles may be abutting without overlap, or have overlapping edge margin regions of for example 1, 2, 3, 4, 5, 6, 7, 8, 9 or 10 pixels wide so that the output patches of the CNN can be stitched together taking account of any discrepancies. Our approach can however, if desired, also be applied to a random sample of patches over the WSI which are of the same or different magnification, as in the prior art, or as might be carried out by a pathologist.

Our neural network is similar in design to the VGG-16 architecture of Simonyan and Zisserman 2014. It uses very small 3×3 kernels in all convolutional filters. Max pooling is performed with a small 2×2 window and stride of 2. In contrast to the VGG-16 architecture, which has a series of fully connected layers after the convolutional layers, we follow the convolution layers with a sequence of "deconvolutions" (more accurately transpose convolutions) to upscale the output image so its dimensions match those of the input image. This type of upsampling has previously been used for natural image processing by Long et al 2015, the full contents of which are incorporated herein by reference.

Each deconvolutional layer enlarges the input feature map by a factor of two in the width and height dimensions. This counteracts the shrinking effect of the maxpool layers and results in output images of the same size as the input images. The output from each convolution and deconvolutional layer is transformed by a non-linear activation layer. At present, the non-linear activation layers use the rectifier function ReLU (x)=max (0, x)ReLU(x)=max(0,x). Different activation functions may be used, such as ReLU, leaky ReLU, eLU, etc. as desired.

The proposed method can be applied without modification to any desired number of tissue types. The constraint is merely the availability of a suitable number and variety of histological images for the tissue type to be learnt by the neural network. The histological images do not need prior expert review other than to establish that the images are representative of healthy tissue, or at least tissue that has not been treated with any compound which it may in future wish to be tested against.

It will be appreciated that the number of convolution and deconvolution layers can be increased or decreased as desired and subject memory limitations of the hardware running the neural network.

We train the neural network using mini-batch gradient descent. The learning rate is decreased from an initial rate of 0.1 using exponential decay. We prevent neural network overfitting by using the "dropout" procedure described by Srivastava et al 2014, the full contents of which are incorporated herein by reference. Training the network may be done on a GPU, CPU or a FPGA using any one of several available deep learning frameworks. For our current implementation, we are using Google Tensorflow, but the same neural network could have been implemented in another deep learning framework such as Microsoft CNTK.

The autoencoder neural network outputs image tiles of size N×N×C, where N is the width and height in pixels of the input patches and C is the number of channels in the input image. For each pair of input and output image tiles a distance metric such as Earth mover's distance (EMD) is computed. If the distance metric is above an empirically determined threshold T, pixels corresponding to the location of the tile in the input image are marked as positive for toxic effects in an output map of size W×H×1, where W and H are the width and height of the original WSI.

While the above description of a particular implementation for our invention has concentrated on a specific approach using one particular autoencoder CNN, it will be understood that our approach can be implemented in a wide variety of different types of autoencoder convolutional neural network. In general, any autoencoder neural network that uses convolution to detect increasingly complex features and subsequently uses transpose convolutions ("deconvolutions") to upscale the feature maps back to the width and height of the input image should be suitable.

Example

Figure 2A:
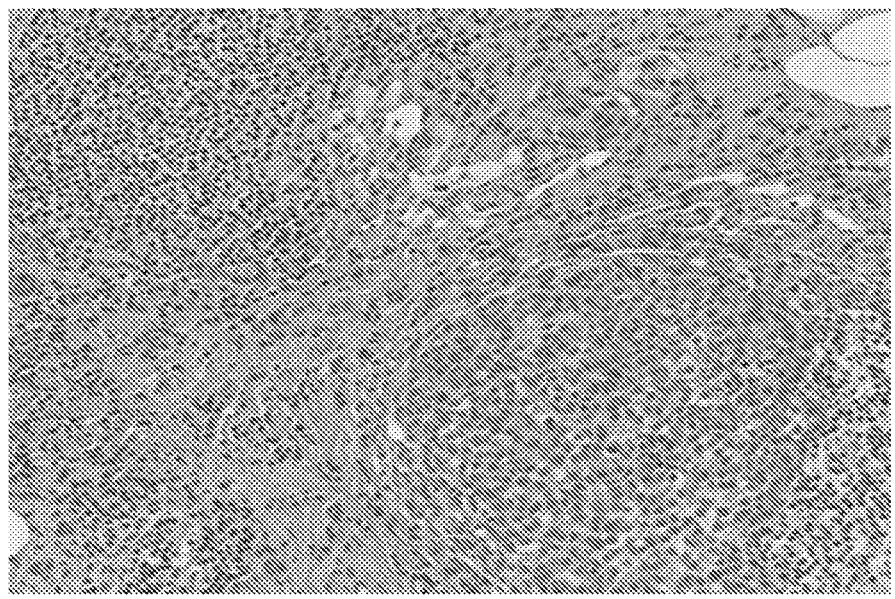
FIG. 2A is a drawing showing a raw pathology image according to an embodiment and in operation this image is in color.

FIG. 2A shows a portion of a raw image as a patch from an H&E-stained WSI in which the cluster of larger, dark purple cells in the bottom right quadrant is a tumor, while the smaller dark purple cells are lymphocytes.

Figure 2B:
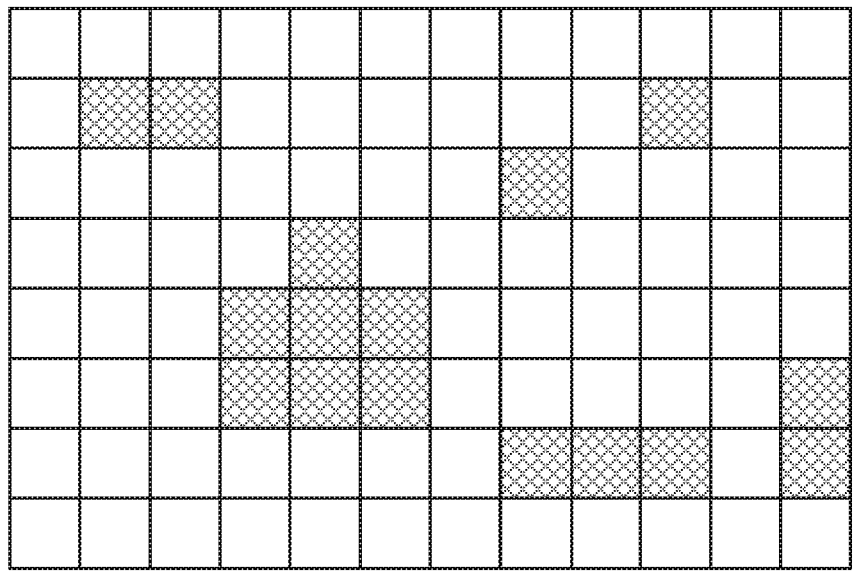
FIG. 2B is a drawing showing the predicted areas of interest generated by the CNN according to an embodiment.

FIG. 2B shows the predicted areas of interest generated by the CNN as a mask. FIG. 2B is a schematic representation of a binary mask as could be generated by our CNN where the binary mask is based on non-overlapping image tiles, with the cross-hatched tiles being the areas of interest and the unhatched tiles are areas that are predicted not to be of interest. It will be understood that if a tile-based approach is taken, the number of tiles would typically much higher than the 12×8 array shown, e.g. by an order of magnitude. In other examples, the areas of interest may have their perimeters configured to follow a shape-based segmentation algorithm, and so represent an arbitrary shape rather than squares or rectangles.

Acquisition & Image Processing

The starting point of the method is that a tissue sample has been sectioned, i.e. sliced, and adjacent sections have been stained with different stains. The adjacent sections will have very similar tissue structure, since the sections are thin, but will not be identical, since they are of different layers.

For example, there could be 5 adjacent sections, each with a different stain, such as ER, PR, p53, HER2, H&E and Ki-67. A microscope image is then acquired of each section. Although the adjacent sections will have very similar tissue shapes, the stains will highlight different features, e.g. nucleus, cytoplasm, all features by general contrast enhancement etc.

The different images are then aligned, warped or otherwise pre-processed to map the coordinates of any given feature on one image to the same feature on the other images. The mapping will take care of any differences between the images caused by factors such as slightly different magnifications, orientation differences owing to differences in slide alignment in the microscope or in mounting the tissue slice on the slide, and so forth.

It is noted that with a coordinate mapping between different WSIs of a set comprising differently stained adjacent sections, the WSIs can be merged into a single composite WSI from which composite patches may be extracted for processing by the CNN, where such composite patches would have dimensions N×N×3m, where 'm' is the number of composited WSIs forming the set.

Some standard processing of the images is then carried out. These image processing steps may be carried out on the WSI level or at the level of individual image patches. The images may be converted from color to grayscale if the CNN is configured to operate on monochrome rather than color images. The images may be modified by applying a contrast enhancement filter. Some segmentation may then be performed to identify common tissue areas in the set of images or simply to reject background that does not relate to tissue. Segmentation may involve any or all of the following image processing techniques:

1. Variance based analysis to identify the seed tissue areas
2. Adaptive thresholding
3. Morphological operations (e.g. blob analysis)
4. Contour identification
5. Contour merging based on proximity heuristic rules
6. Calculation of invariant image moments
7. Edge extraction (e.g. Sobel edge detection)
8. Curvature flow filtering
9. Histogram matching to eliminate intensity variations between serial sections
10. Multi-resolution rigid/affine image registration (gradient descent optimizer)
11. Non-rigid deformation/transformation
12. Superpixel clustering It will also be understood that image processing steps of the above kind can be carried on the WSIs or on individual patches after patch extraction. In some cases, it may be useful to carry out the same type of image processing both before and after patch extraction, i.e. as CNN pre-processing and CNN post-processing respectively. That is, some image processing may be done on the WSI before patch extraction and other image processing may be done on a patch after its extraction from the WSI.

These image processing steps are described by way of example and should not be interpreted as being in any way limitative.

Training & Prediction

Figure 3:
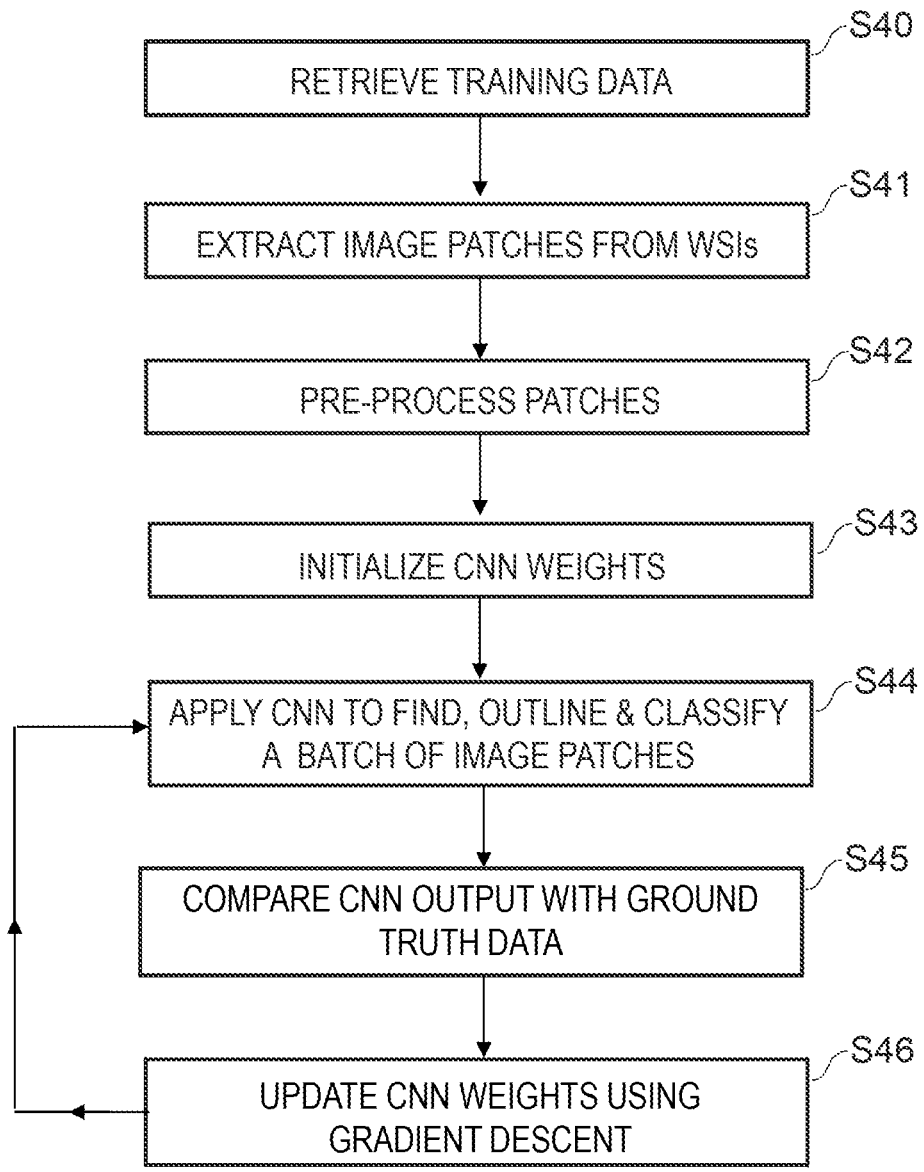
FIG. 3 is a flow diagram showing the steps involved in training the CNN.

FIG. 3 is a flow diagram showing the steps involved in training the CNN.

In Step S40, training data is retrieved containing WSIs for processing which have been previously reviewed by at least one clinician and the review session has been logged to record relevant parameters relating to the clinician's interaction with the WSI. The training data set comprises histological images and pathologist interaction data. The pathologist interaction data comprises a plurality of parameters relating to how a pathologist has interacted with one or more visualizations of a given histological image that is contained in the training data set. Suitable parameters include any combination of the following:

- viewing time of a pixel and viewing magnification of a pixel;
- pixels at locations or areas on the histological images associated with pathologists' annotations; and
- pixels at locations or areas on the histological images that were subject to a user command to view at higher magnification.
- mouse (or other pointer) click information (e.g. pixel coordinates, magnification level, timestamp),
- zoom peaks, i.e. areas in the slide that the pathologist zoomed in to full magnification (native resolution of the WSI) multiple times
- slow panning zones, i.e. zones which the pathologist moved across slowly
- fixation zones, i.e. zones where the pathologist spent longer amounts of time looking, Moreover, compound parameters may be generated when a given histological image includes interactions from multiple pathologists. In that case, a parameter based on a correlation factor between interaction with the same histological image from multiple pathologists can be computed, for example to highlight when the same area is looked at in detail by multiple pathologists, compared to an area that has only been looked at in detail by one pathologist.

In Step S41, the WSIs are broken down into image patches, which are the input image patches for the CNN. That is, image patches are extracted from the WSI.

In Step S42, the image patches are pre-processed as described above. (Alternatively, or in addition, the WSIs could be pre-processed as described above prior to Step S41.)

In Step S43, initial values are set for the CNN weights, i.e. the weights between layers.

In Step S44, each of a batch of input image patches is input into the CNN and processed to find and classify the patches on a pixel-by-pixel basis.

In Step S45, the CNN output image patches are compared with the ground truth data. This may be done on a per-patch basis. Alternatively, if patches have been extracted that cover the entire WSI, then this may be done at the WSI level, or in sub-areas of the WSI made up of a contiguous batch of patches, e.g. one quadrant of the WSI. In such variants, the output image patches can be reassembled into a probability map for the entire WSI, or contiguous portion thereof, and the probability map can be compared with the ground truth data both by the computer and also by a user visually if the probability map is presented on the display as a semi-transparent overlay to the WSI, for example.

Figure 4:
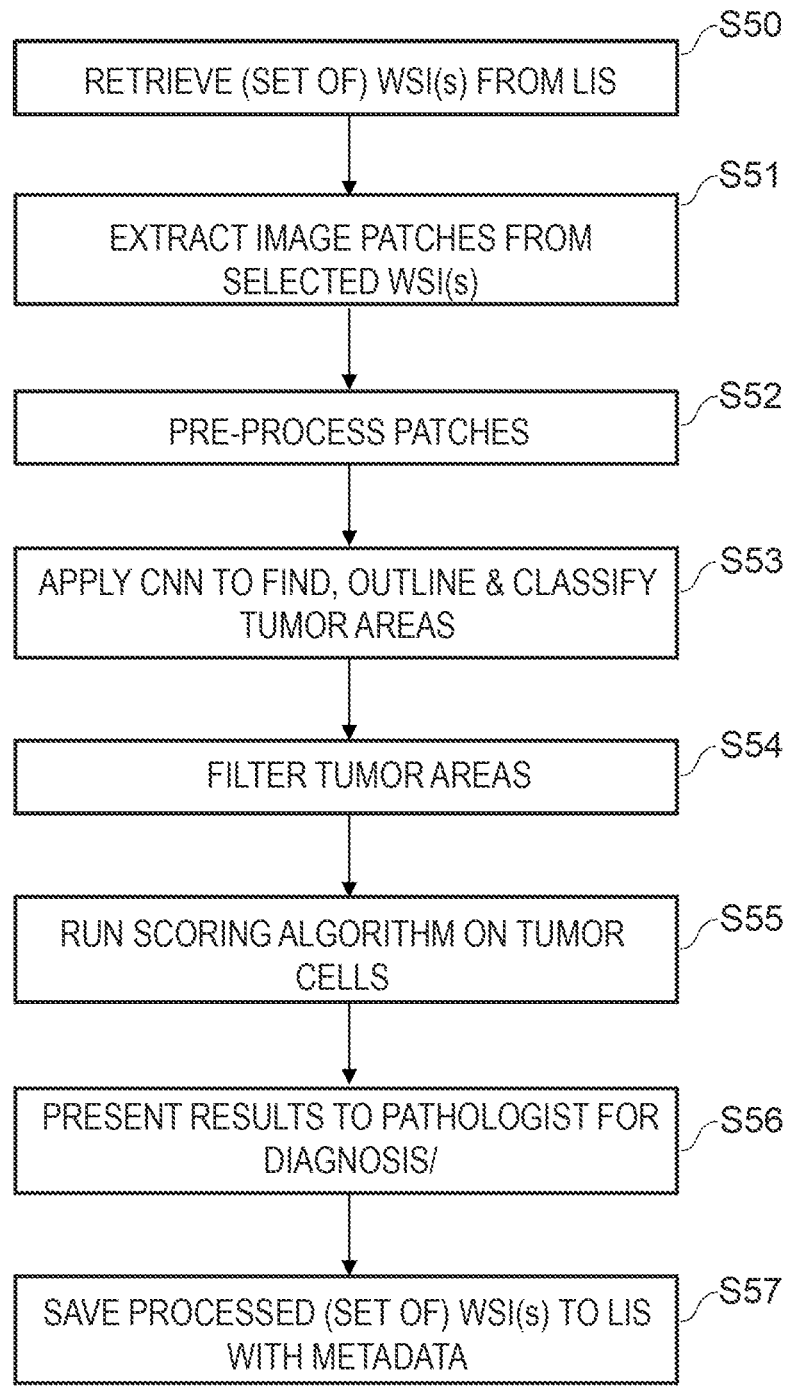
FIG. 4 is a flow diagram showing the steps involved in prediction using the CNN.

In Step S46, the CNN then learns from this comparison and updated the CNN weights, e.g. using a gradient descent approach. The learning is thus fed back into repeated processing of the training data as indicated in FIG. 4 by the return loop in the process flow, so that the CNN weights can be optimized.

After training, the CNN can be applied to WSIs independently of any ground truth data, i.e. in live use for prediction.

An alternative embodiment of FIG. 3 will now be described. In this alternative embodiment, FIG. 3 is a flow diagram showing the steps involved in training the autoencoder CNN.

In Step S40, training data is retrieved containing WSIs for processing. The learning is self-supervised, so there is no need for ground truth data, such as expert annotations, expert segmentation and so forth.

In Step S41, the WSIs are broken down into image patches, which are the input image patches for the CNN. That is, image patches are extracted from the WSI.

In Step S42, the image patches are pre-processed as described above. (Alternatively, or in addition, the WSIs could be pre-processed as described above prior to Step S41.)

In Step S43, initial values are set for the CNN weights, i.e. the weights between layers.

In Step S44, each of a batch of input image patches is input into the CNN and processed on a pixel-by-pixel basis as described further above with reference to FIGS. 1A and 1B.

In Step S45, the CNN output image patches are compared to the CNN input image patches. This may be done on a per-patch basis. Alternatively, if patches have been extracted that cover the entire WSI, then this may be done at the WSI level, or in sub-areas of the WSI including a contiguous batch of patches, e.g. one quadrant of the WSI. In such variants, the output image patches can be reassembled into a probability map for the entire WSI, or contiguous portion thereof.

In Step S46, the CNN then learns by aiming to minimize the difference between the input and output patches by iteratively updating the CNN weights, e.g. using a gradient descent approach. The self-supervised learning is thus fed back into repeated processing of the training data as indicated in FIG. 2 by the return loop in the process flow, so that the CNN weights can be optimized.

After training, the CNN can be applied to WSIs, i.e. in live use for anomaly detection. FIG. 4 is a flow diagram showing the steps involved in prediction using the CNN.

In Step S50, one or more WSIs are retrieved for processing, e.g. from a laboratory information system (LIS) or other histological data repository. The WSIs are pre-processed, for example as described above.

In Step S51, image patches are extracted from the or each WSI. The patches may cover the entire WSI or may be a random or non-random selection.

In Step S52, the image patches are pre-processed, for example as described above.

In Step S53, each of a batch of input image patches is input into the CNN and processed to find and classify the patches on a pixel-by-pixel basis as described further above with reference to FIGS. 1 and 2. The output patches can then be reassembled as a probability map for the WSI from which the input image patches were extracted. The probability map can be compared with the WSI both by the computer apparatus in digital processing and also by a user visually, if the probability map is presented on the display as a semi-transparent overlay on the WSI or alongside the WSI, for example.

In Step S54, the areas of interest are filtered excluding areas of interest that are likely to be false positives, for example areas that are too small or areas that may be edge artifacts.

In Step S55, a scoring algorithm is run. Computing the score may involve application of a filter, either to filter out certain pixels or groups of pixels (e.g. tiles) prior to application of a scoring formula (which would be part of Step S54), or application of a filter after a scoring formula has been applied to modify the scores (which would be part of Step S55). The scoring may be aggregated for each area of interest, and/or further aggregated for the WSI (or a sub-area of the WSI). One useful kind of sub-area for aggregating scores may be an image tile (or group of image tiles) in the case that the data set for the WSI is stored in memory in neighboring image tiles, i.e. in a two-dimensional array of non-overlapping or overlapping rectangular or square tiles, where in the case of an overlap this is typically a relatively small overlap at the margins. In that way, a decision on whether to pre-cache an image tile may be made taking account of the score for that image tile.

In Step S56, the results are presented to a pathologist or other relevantly skilled clinician for review and diagnosis, e.g. by display of the annotated WSI on a suitable high-resolution monitor.

In Step S57, the results of the CNN, i.e. the probability map data and optionally also metadata relating to the CNN parameters together with any additional diagnostic information added by the pathologist, are saved in a way that is linked to the patient data file containing the WSI, or set of WSIs, that have been processed by the CNN. The patient data file in the LIS or other histological data repository is thus supplemented with the CNN results.

In summary, the trained CNN has taken as input pixels from a digital, i.e. virtual, slide image and has computed a score, e.g. as a score ratio in the range of 0 to 1. That score indicates how relevant an area should be to a pathologist based on what the CNN has learnt from its training data relating to how pathologists interact with virtual slide images when using a visualization application.

As described below, the score outputs can be assembled, e.g. to create a heatmap of areas of interest, mapping each input slide area to its score. Pixels of interest that are touching or are in close proximity to each other may be grouped by a segmentation algorithm to determine individual areas of interest. For each area, a score may be computed as the mathematical average over all the probabilities of pixels in a segmented area covering a group of pixels. Some other summary statistic such as median, weighted average, etc. may also be used to compute a score for an area.

Enhanced Graphical User Interface Using Areas of Interest

Figure 5:
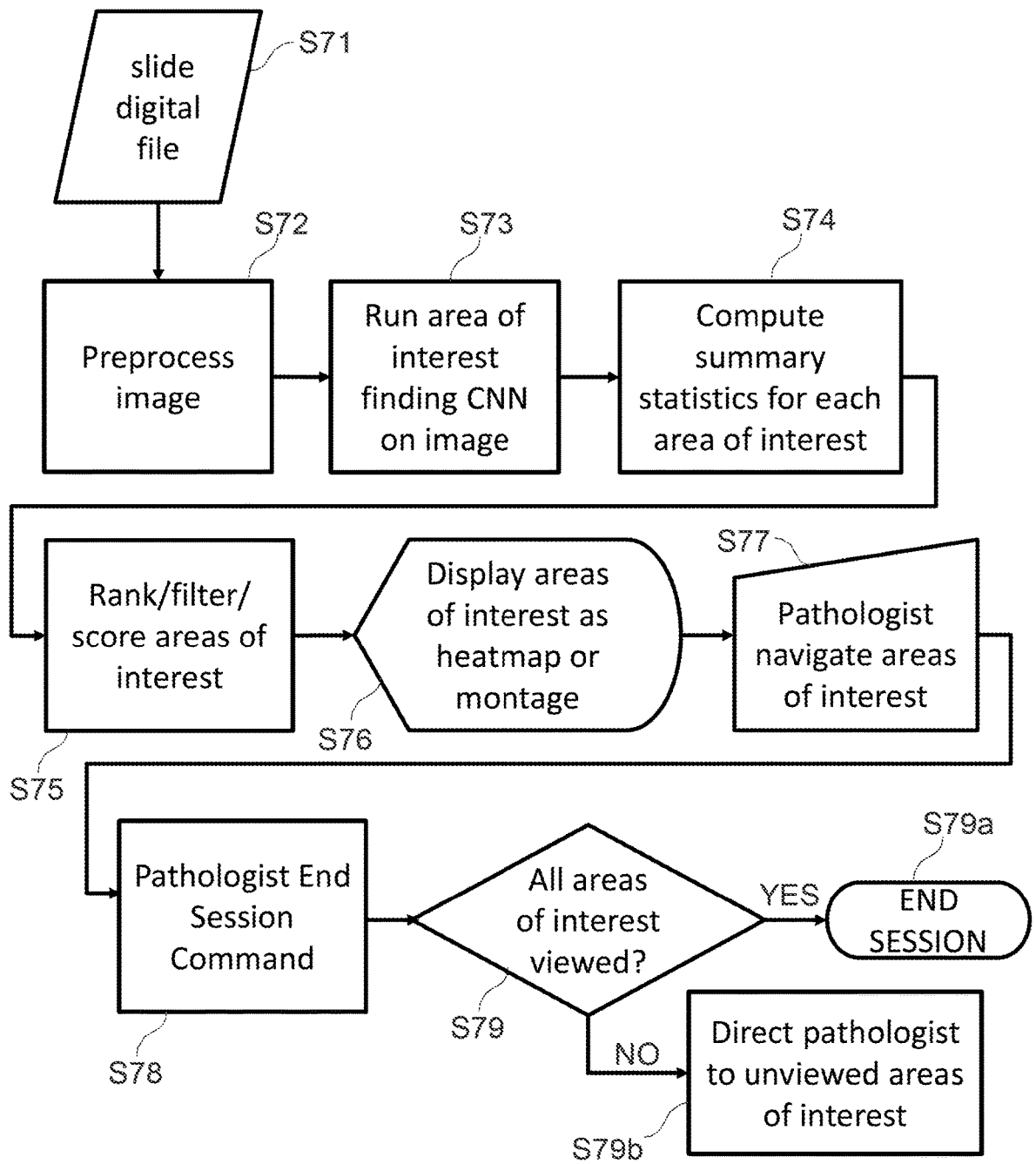
FIG. 5 is a flow diagram of a method according to one embodiment of the present disclosure.

FIG. 5 is a flow diagram according to an embodiment of the disclosure as performed by a visualization application with a GUI that supports the areas of interest found by the trained CNN as described above.

Step S71 provides an image data file containing image data of a WSI, as may have been generated by a slide scanner. It will be appreciated the image data file may include multiple images, e.g. one for each of a plurality of stains, or one for each of a different depth in the sample (a so-called z-stack) obtained by stepping the focal plane of the microscope through a transparent or semi-transparent sample of finite depth.

Step S72 is an optional step where some CNN pre-processing may be performed, as described by way of example further above, such as variance-based analysis, adaptive thresholding, morphological operations and so forth.

Step S73 runs the above-described CNN, in particular as described with reference to Steps S51 to S54 of FIG. 4. A pixel-by-pixel classification of tissue type is performed to mark pixels of interest, followed by segmentation to outline areas of interest. For the segmentation, it is generally the case that contiguous of-interest pixels, i.e. ones that are touching each other or in close proximity to each other, belong to a common area of interest. More complex segmentation criteria will however usually be included to improve reliability, e.g. to identify two touching areas of interest with different pixel classifications, e.g. associated with two different of-interest classifications. The CNN assigns each pixel a probability. The individual pixel scores are combined on the basis of individual areas determined by segmentation to determine what areas of interest are to be defined. The areas of interest may be filtered by criteria set in the software application, which may be pre-set and may optionally also be adjustable by a user, e.g. a pathologist may choose to see only areas of interest above 100 micrometers in diameter that have average interest scores above 50%. Another pathologist may want to examine only areas with average interest scores above 80%.

In Step S74, the data generated by the area-of-interest-finding CNN in Step 73, i.e. the area-of-interest-specific data, is used to compute a set of summary statistics for each area of interest. For example, for each area of interest, a score may be computed as the mathematical average of the above-mentioned probability values for all the pixels contained in that area of interest. Some other summary statistic such as median, weighted average, etc. may also be used to compute a score. The set of summary statistics may include for example dimensional or morphological attributes of an area of interest, such as total area as measured by the number of pixels or shape of the area of interest, or prevalence of a certain pixel classification when there are multiple of-interest pixel classes. Areas of interest are not necessarily from a single slide; they may belong to separate slides, e.g. the tissue samples of two slides may be stained with different stains and thus highlight different classes of tumor cells, so that some areas of interest are associated with a first slide and other areas of interest with a second slide. In other implementations, the score can be computed using traditional image processing techniques applied to the areas of interest identified by the CNN. For example, shape and texture measures can be used to create a set of statistical measures to include in the summary statistics. Optionally Step S74 additionally carries out a filtering of the areas of interest based on the summary statistics. For example, the filter, which may be configured by the pathologist or be pre-set, may choose to pass only areas of interest with a maximum dimension above a threshold value, e.g. 100 micrometers.

Step S75 takes the set of areas of interest passed by Step S74 and ranks them in order. A ranking of the areas of interest can then be carried out based on the summary statistics and applying a set of criteria. Pre-sets of standard ranking approaches may be provided to the user, allowing the user to select on the basis of the pre-sets. Moreover, the user may be provided with a user interface to define which criteria are to be applied. In the case of scalar valued criteria, e.g. based on a length dimension or area or an integer count (e.g. number of pixels), the user may set threshold values, or value ranges for these criteria. The ranking order may be based on a composite score, or be a simple single parameter ranking, e.g. based on a size parameter of the area of interest such as area or maximum dimension, or a morphological parameter such as aspect ratio. The visualization application then generate a visualization for a display which displays the WSI or a part thereof, or multiple sub-areas in a way that is dependent on the segmentation mask which contains the area-of-interest data as remaining after any filtering. The visualization can also be generated having regard to the ranking, for example so as to include a visual indication of the ranking, e.g. a label or annotation, or in the case that a montage view is created with a list of areas of interest with thumbnail images, the list can be in ranking order, or reverse ranking order, and may also be restricted to the areas of interest that have passed the filter. In some implementations, the visualization includes an overview viewing pane and a segmentation mask viewing pane. The overview viewing pane and a segmentation mask viewing pane may be displayed with the segmentation mask overlaid on, or alongside, the histological image. The visualization application may usefully include a GUI control operable to permit a user to interact with the visualization so as to select one or more of the areas of interest.

The visualization application may also incorporate user tracking, which monitors the same or a similar set of parameters as monitored to compile the training data. Namely, the visualization application may have an agent which monitors a user's interaction with visualizations of the histological image data set to track which of the areas of interest the user has specifically viewed, as decided upon by a logical test, such as one including Boolean operators, threshold tests and/or composite scoring equations using the parameter values of the monitored parameters as operands. The agent can thus keep track of which areas of interest the user has specifically viewed, i.e. viewed in enough detail to warrant a conclusion that the user would have been able to come to a reliable diagnostic conclusion about the area.

In Step S79, based on this session tracking, a checking function may be applied responsive to a user command issued in Step S78 to end a visualization session on a histological image, which performs a check of whether the user has specifically viewed all of the areas of interest, or perhaps all the highest 'n' ranked areas of interest, where 'n' is an integer value that may be pre-set or set by or for the user. When the check indicates the user has not specifically viewed the areas of interest that are fed into the checking function, a notification can be issued to the user, e.g. via a pop-up window, which requires a further confirmation input from the user prior to ending the visualization session in Step S79a, but which also gives the user a second option of reviewing the area or areas of interest that have been missed. In Step S79b, when the check indicates the user has not specifically viewed all areas of interest, the user is guided to view each area of interest that has not yet been specifically viewed, where this guiding could be mandated or optional.

Further details of the options for visualization of the slide image are discussed with reference to how the image data is displayed to the user in a GUI window of a display device. The visualization can take account of the filtering and also the ranking. In particular, what are deemed to be the most relevant areas of interest in the WSI are displayed in a clinically relevant way with their summary statistics also being available either in all cases as part of the overall display, or selectively responsive to a GUI command from the user, e.g. 'clicking' with a cursor on an area of interest in the WSI to generate a pop-up window showing the statistics for that area of interest in tabular or other suitable form. This approach allows areas of interest to be highlighted and presented to the user in a way that provides the user with ranking information among the potentially significant areas of interest as well as statistical summaries of these areas. The statistical summaries can present individual parameter values for each area of interest, in particular those used as filtering and/or ranking criteria, as well as compound parameters such as a ranking number or significance score that are computed from formulaic and/or Boolean logical combinations of multiple filtering and/or ranking criteria.

Typically, the image displayed will either be in the form of a combined overlay view or a multi-tile view. In an overlay view the raw data (possibly processed) is displayed with the segmentation data overlaid on top, where the segmentation data is translated for the visualization into shading and/or outlining. If there are multiple classes for of-interest areas, the shading or outlining may be color-coded by classification. Another possibility if there are multiple of-interest classes is to represent the segmentation data as a heat map (in color or gray scale) or contour map (with contour lines).

Areas that are not of interest may not be marked at all, or may be shaded with a color or monochrome wash of high transparency, e.g. a blue wash or a gray wash. In a multi-tile view, what were the different layers in the overlay view are displayed side-by-side as tiles, so there will be a tile showing raw image data (possibly processed) and segmentation data of the areas of interest. If desired a separate segmentation data tile may be displayed for each of-interest classification type in the case of multiple of-interest classes. The presentation of the areas of interest in the display takes account of the filtering and/or ranking performed in Step S75. Factors such as the area scores, the classification type of the area of interest and any other parameters in the summary statistics associated with areas of interest can be used singly or in combination to configure the display.

There are several options for displaying the detected, filtered and ranked areas of interest to the user.

In a WSI view, one way to display the area-of-interest information is to overlay a series of markers over a low-resolution image of the WSI. The markers will be sorted. A pathologist is provided with suitable GUI tools for navigating through the areas of interest by ranking of their perceived level of interest, both from higher ranked areas of interest to lower ranked areas of interest and the reverse order. Suitable GUI tools include: keyboard shortcuts; keyboard up and down, or left and right, arrow keys, keyboard page up and page down keys, mouse navigation (e.g. scrolling up or down with a scroll wheel) or other input devices (voice navigation, multitouch gesture in a touch sensor, etc.). Selecting the ranking marker in the GUI may prompt display of that area's summary statistics, or a subset thereof, and/or display of a higher resolution view of the area of interest either in a pop-up linked to the display of the tumor in the low-resolution image, or in a separate, higher resolution viewing pane. The user may cause display of a high, e.g. full native, resolution image of the area of interest by a suitable GUI command, such as a keyboard command, a mouse command (e.g. double-click) or other suitable input. A corresponding GUI command is provided to navigate back to a low-resolution WSI view. The visualization application preferably provides GUI controls that permit the user to step through the areas of interest up or down by ranking order in both low-resolution and high-resolution views.

One example WSI view would be for all areas of interest that have passed the filter of Step S75 to be displayed (i.e. their segmentation data displayed), together with a ranking marker label 1, 2, 3 etc. Clicking on the ranking marker label may then generate a pop-up listing a selected set of the summary statistics, in particular those that are used by the filter and/or a thumbnail view of the area of interest at a resolution higher than that in the WSI view. Alternatively, the view may be a split-screen view with the overlay image or image tiles being displayed in one part of the screen and a table of the filtered areas of interest in another part of the screen. The table may be presented initially sorted by ranking, but the GUI may also have the facility to be user re-sortable by any other column, or combination of multiple columns, where the other columns may be any criterion from the summary statistics or filter criteria, such as total area of an area of interest, classification of an area of interest etc. For example, the sorting could be by of-interest classification followed by total area. In the case of a multi-slide image file, the sorting could be by slide number followed by some other parameter(s).

In a multi-resolution view comprising one viewing pane at lower resolution (e.g. 10× magnification), typically reproducing a WSI, and another viewing pane at higher resolution (e.g. 60× magnification, i.e. 6× or 600% zoom relative to the 10× view). For example, the initial view presented may be a WSI low resolution image pane and a high resolution image pane centered on the area of interest with the top ranking. A step-through down arrow (or pair of down and up arrows) or other suitable GUI button or button combination, such as a physical or virtual scroll wheel, may then allow the user to step through the filtered areas of interest by ranking one by one. The GUI may allow the user to adjust the resolution in the high resolution image pane through user input. The GUI may also select the initial resolution for the high resolution image pane so that the area of interest is sized to substantially fill the high resolution viewing pane.

The visualization application may thus determine what is displayed to the user, what areas of interest are highlighted with segmentation data and summary statistics and, in the case of a selective view, the time sequence, i.e. order, in which the areas of interest are displayed to the user.

Another way of displaying areas of interest that is particularly suited to slide sets is to create a montage where low-resolution images of the areas of interest along with their summary statistics are displayed as sorted tiles. The sorting may be by way of displaying a one-dimensional (1D) list, or a two-dimensional (2D) grid. It is even possible to arrange the areas of interest in three dimensions, e.g. with the aid of virtual reality goggles. The user may navigate the 1D list or 2D tile array using keystrokes, mouse scrolling or other input modalities (voice, touch, etc.). Once a tile is selected the pathologist can quickly navigate to a high-resolution version of the area of interest in the appropriate slide to make a more in-depth review of that area of interest optionally with reference to the results of the CNN analysis as presented by the summary statistics and segmentation data. The method may be further extended once a pathologist has found a tumor in an area of interest to allow the pathologist to perform further numerical processing on the tumor by applying one or more further analysis algorithms to the tumor that may assist diagnosis.

After viewing the filtered and ranked areas of interest, the pathologist has the further option of selecting any one of these areas of interest (or any subset of the ranked areas of interest, or indeed the full set of filtered areas of interest) for further study. By further study we mean applying one or more additional algorithms to provide further information on a selected area of interest to assist with diagnosis.

The determined areas of interest, optionally after filtering and/or ranking, can be presented in the GUI by overlaying a series of markers onto a low-resolution image of the whole virtual slide, or at least a large proportion thereof. The markers may contain some visual indication of ranking. A GUI control may be provided to allow a user to navigate up or down the areas of interest in ranking order using a suitable input, for example, keyboard shortcuts (such as arrow keys), mouse navigation (scrolling) or other inputs (voice navigation via an audio input, touch gestures via a touch screen, etc.). The GUI may be configured so that, when a marker is selected, the summary statistics for the area of interest are displayed along with a higher resolution image of the area. The summary statistics and higher resolution image may be shown in the same popup window, or in respective popup windows, where the popup high-resolution image may be a thumbnail-type crop. Another option is to have a split-screen view with one area of the display showing the low-resolution image, and another area of the display showing whichever area is selected with a higher-resolution image. Pathologists may choose to view the full resolution area by tapping a key on the keyboard, double-clicking on the mouse or other equivalent actions. A similar action will quickly return the pathologist to the low-res view. The pathologist may navigate the list either in the low-resolution or the high-resolution viewing window.

One or multiple areas may be selected by the pathologist for additional processing by the pathologist or by additional algorithms.

In summary, the visualization is configured to prompt the user to examine areas in the image that are likely to be of clinical interest as determined by the trained CNN, which has been trained with training data generated by monitoring how an expert user has interacted with a WSI using a visualization application. The areas of interest are defined by applying segmentation to the output of the trained CNN. In particular, compared with a traditional visualization application, the proposed marking of areas of interest serves to support a user in making an initial rough, manual visual scan over the whole slide area at low resolution as well as prompting the user to view certain areas, namely the areas of interest, at higher resolution. The automated pre-processing of the visualization presented to the pathologist based on CNN-aided filtering and ranking as described can reduce the amount of time needed by the pathologist to review a slide as well as reducing the chance that a review of a clinically important area is missed as a result of human error.

Pre-Fetching and Pre-Caching of Areas of Interest

Figure 6:
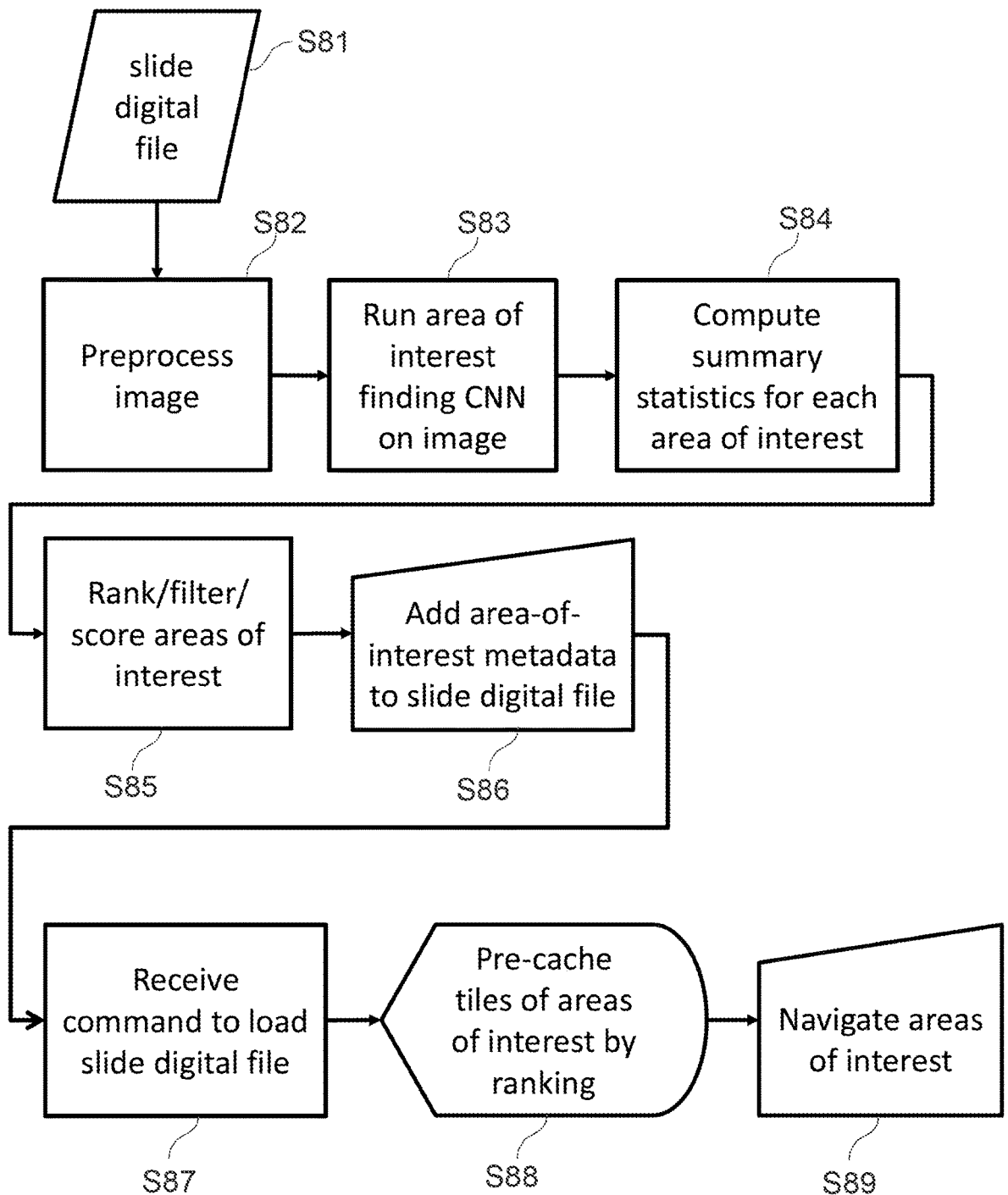
FIG. 6 is a flow diagram of a method according to another embodiment of the present disclosure.

FIG. 6 is a flow diagram according to an embodiment of the disclosure in which selective pre-fetching or pre-caching of areas of interest is performed, based on the areas of interest found by the CNN method as described above.

Step S81 provides access to an image data file containing image data of a WSI, as may have been generated by a slide scanner. It will be appreciated the image data file may include multiple images, e.g. one for each of a plurality of stains, or one for each of a different depth in the sample (a so-called z-stack) obtained by stepping the focal plane of the microscope through a transparent or semi-transparent sample of finite depth.

Step S82 is an optional step where some CNN pre-processing may be performed, as described by way of example further above, such as variance-based analysis, adaptive thresholding, morphological operations and so forth.

Step S83 runs the above-described CNN, in particular as described with reference to Steps S51 to S54 of FIG. 4. A pixel-by-pixel classification of tissue type is performed to mark pixels of interest, followed by segmentation to outline areas of interest. For the segmentation, it is generally the case that contiguous of-interest pixels, i.e. ones that are touching each other or in close proximity to each other, belong to a common area of interest. More complex segmentation criteria will however usually be included to improve reliability, e.g. to identify two touching areas of interest with different pixel classifications, e.g. associated with two different of-interest classifications. The CNN assigns each pixel a probability.

In Step S84, the data generated by the area-of-interest-finding CNN in Step 73, i.e. the area-of-interest-specific data, is used to compute a set of summary statistics for each area of interest. For example, for each area of interest, a score may be computed as the mathematical average of the above-mentioned probability values for all the pixels contained in that area of interest. Some other summary statistic such as median, weighted average, etc. may also be used to compute a score. The set of summary statistics may include for example dimensional or morphological attributes of an area of interest, such as total area as measured by the number of pixels or shape of the area of interest, or prevalence of a certain pixel classification when there are multiple of-interest pixel classes. Areas of interest are not necessarily from a single slide; they may belong to separate slides, e.g. the tissue samples of two slides may be stained with different stains and thus highlight different classes of tumor cells, so that some areas of interest are associated with a first slide and other areas of interest with a second slide. In other implementations, the score can be computed using traditional image processing techniques applied to the areas of interest identified by the CNN. For example, shape and texture measures can be used to create a set of statistical measures to include in the summary statistics. Optionally Step S84 additionally carries out a filtering of the areas of interest based on the summary statistics. For example, the filter, which may be configured by the pathologist or be pre-set, may choose to pass only areas of interest with a maximum dimension above a threshold value, e.g. 100 micrometers.

Step S85 takes the set of areas of interest passed by Step S84 and ranks them in order. A ranking of the areas of interest can then be carried out based on the summary statistics and applying a set of criteria. Pre-sets of standard ranking approaches may be provided to the user, allowing the user to select on the basis of the pre-sets. Moreover, the user may be provided with a user interface to define which criteria are to be applied. In the case of scalar valued criteria, e.g. based on a length dimension or area or an integer count (e.g. number of pixels), the user may set threshold values, or value ranges for these criteria. The ranking order may be based on a composite score, or be a simple single parameter ranking, e.g. based on a size parameter of the area of interest such as area or maximum dimension, or a morphological parameter such as aspect ratio.

Step S86 then adds metadata derived from Steps S82 to S85 to the slide digital file, so the slide digital file not only includes the histological image data set, but also metadata identifying the areas of interest as defined by the CNN and subsequent segmentation.

When a visualization application, or some other application that wishes to process the histological image data set, issues a command to retrieve the image data from the slide digital file, the metadata can then be used as a basis for deciding the order in which different portions of the image data are loaded from high latency storage into low latency storage.

Loading of the image data, with or without other types of data contained in the slide digital file, may be in the context of a network in which the slide digital files are stored in a data repository or library, typically as a database, on a remote server, and the visualization application (or at least a thin client thereof) is running on a client computer connected to the data repository over a network connection, such as in a hospital network. The high latency storage in this case is the library, and the low latency storage is the client computer's local storage.

In Step S87, a computer apparatus loaded with a visualization application operable to interactively display histological images of histological image data sets to a user receives a command, e.g. from the user, to load a certain slide digital file from a virtual slide library. Once a network connection has been established to the slide library, e.g. by a network connector of the computer apparatus, transfer of data between the slide library and the computer apparatus can take place. Executing the user load command may involve initially checking whether the requested slide digital file includes area-of-interest metadata as generated by the above-described Steps S82 to S85. If not, then this metadata may be generated by causing the method of Steps S81 to S86 to be carried out on the slide digital file.

As shown by Step S88, if the slide digital file includes area-of-interest metadata, the retrieval of the image data may proceed by first transferring small-area sub-images of the data set that contain the areas of interest before loading other sub-images that do not contain any areas of interest, where this proactive retrieval of image data relating to areas-of-interest may be referred to as pre-fetching. The small-area sub-images may be loaded at native resolution as stored in the record at the data repository or in stages at increasing resolution steps, e.g. from ×5 to ×50 in, for example the steps of ×5, ×20, ×40, ×60. Usually, a low-resolution large area version of the WSI is transferred to the client computer prior to starting to transfer any of the high-resolution sub-images. In embodiments in which the metadata includes a ranking for the areas of interest, the small-area sub-images may be loaded having regard to ranking order. Moreover, the small-area sub-images that are loaded may be dictated by the storage structure of the slide digital file. Some virtual slide images are obtained by a scan with a single high-resolution objective 60×, but are stored not only in 60× resolution, but also in one or more stepped down lower resolutions which have been computed from the high resolution image data, e.g. 40× 20× and 5×. Moreover, each resolution tier of image data stored in a slide digital file may be stored in tiles of a fixed memory size, e.g. tiles of 256×256 or 512×512 pixels. The transfer of small-area sub-images may thus take place in units of these tiles, so that if an area of interest includes at least one pixel from a certain tile, then that tile is loaded together with other tiles including one or more pixels from that area of interest.

Loading of the image data may also be in the context of a single computer apparatus, where the storage has two or more latency levels, e.g. as represented in decreasing latency order by local disk storage, mass RAM storage, cache RAM storage, numerical (central) processor cache memory and graphics processor cache memory. Cache memory is high-speed static random access memory (SRAM) associated with a processor or processor cluster, such as a CPU, GPU or TPU, which has a faster access time for the processor or processor cluster than other RAM which the processor or processor cluster can access. In other words, the loading may be optimized with a computer apparatus whose memory is composed of a plurality of memory tiers arranged in a hierarchy of increasing latency, wherein at least the lowest latency memory tier is a cache tier. When the computer apparatus is running a visualization application, and the visualization application issues a command to view a histological image data set which is already loaded into the memory of the computer apparatus, the different latency levels of the computer memory may be managed with reference to the area-of-interest metadata associated with the requested histological image data set. A cache policy may be adopted by the computer apparatus which preferentially loads into, and/or preferentially retains in, one or more of the lower latency cache tiers, high-resolution small-area sub-images of the data set containing the areas of interest, where the preference is compared to other small-area sub-images that do not contain any areas of interest, or areas of lesser interest in the case that the metadata includes ranking order, so that high ranking maps to lower latency and/or preferential cache retention.

As shown with Step S89, when a user navigates the virtual slide in the visualization application, the pre-fetching over the network or the pre-caching as part of a computer's cache policy, as described above, will overall reduce the wait times of the user before high-resolution sub-images requested by the user are displayed, since these will more often than not have been pre-fetched or pre-cached, or at least pre-fetching or pre-caching will have started, before the user request is issued.

Various modifications may be envisaged. For example, the training data may incorporate monitoring of how each individual user reviews a WSI, and so may build up spatial sequence patterns of how users tend to review a WSI. The ranking order of the areas of interest may therefore not be optimized, or not only be optimized, by clinical relevance (e.g. as measured by how long a user looks at a particular area at highest available resolution), but rather may be optimized for the time order in which the user is expected to review each area of interest during a session. For example, users may tend to follow a raster-like pattern of left-to-right row scans from top to bottom of a WSI, or zig-zag horizontal scans from top to bottom. In that way, the pre-fetching or pre-caching may follow the order with which the user is expected to step through his or her review of the areas of interest.

In summary we provide an aid to a pathology image visualization application ('viewer') of the type that handles WSIs on a tile-by-tile basis, i.e. the WSI is broken up into a 2D grid of tiles, and only a small portion of those tiles are displayed on the screen at any one time. The use of tiles reduces the memory requirements of the visualization application to manageable levels, which is crucial when dealing with large WSIs of tens of gigabytes that would crash the application if loaded in their entirety at native resolution. New tiles are loaded and cached into memory from local or network storage as the user navigates across the slide. This approach is an established way of improving the tile rendering speed and enhancing the overall user experience. Our proposed aid to memory management of the tiles makes use of the metadata generated by the CNN to identify areas of interest. This metadata gives the application a-priori knowledge of the areas of interest, which allows the application to adopt a pre-fetching policy (over the network to access the WSI data) and pre-caching policy (within the computer running the visualization application) to reduce the amount of lagging during slide review. The visualization application pre-fetches and pre-caches tiles relating to areas of interest, optionally in ranking order, whenever a user opens a new WSI session. In this way, navigation will overall be faster, since the areas that the user is most likely to visit are already available in memory as the user zooms in to and pans over the areas of interest.

It will be appreciated that the above-described pre-caching or pre-fetching relates to loading at high resolution small-area sub-images that have not been specifically requested by the governing application. Generally, if a visualization application or other application requests that a certain sub-image be loaded at high resolution, then this will take precedence over any pre-loading as performed by the above-described pre-fetching or pre-caching procedures.

Variable Image Compression Based on Areas of Interest

Figure 7:
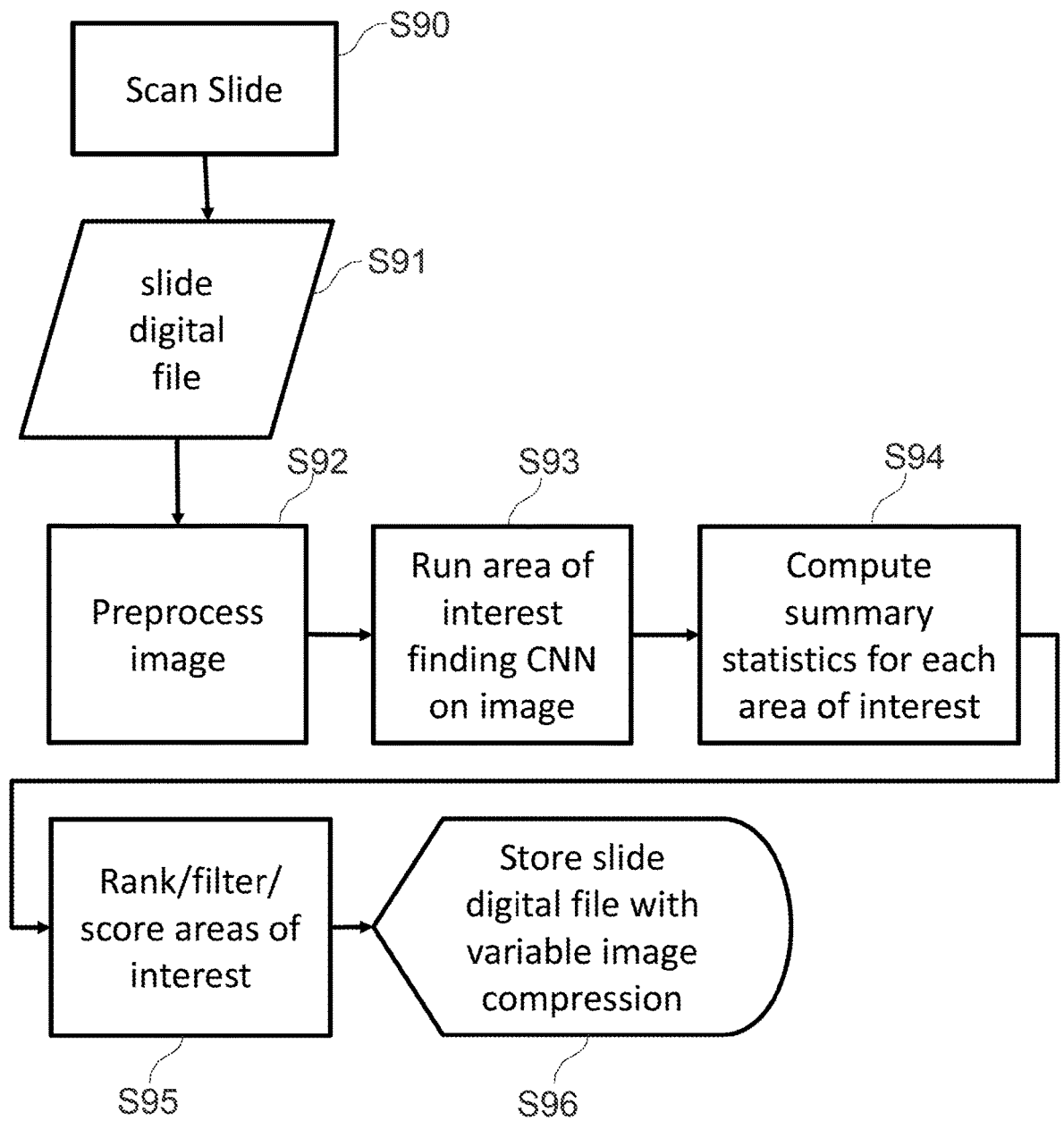
FIG. 7 is a flow diagram of a method according to a still further embodiment of the present disclosure.

FIG. 7 is a flow diagram according to an embodiment of the disclosure as performed by a visualization application with a GUI that supports the areas of interest found by the trained CNN as described above.

Step S90 provides a slide containing a histological sample to a slide scanner. The slide scanner incorporates a microscope module including a slide loader and a high-resolution objective lens. Depending on the design, the microscope module may have multiple objective lenses with different resolutions, and a scan may use only one of the multiple objective lenses or a combination of the objective lenses. The slide scanner may have an integral control computer operable to control the microscope module so as to acquire a histological image data set, or alternatively the slide scanner may be designed to be controlled by a separate control computer, such as a personal computer, connected to the slide scanner by an interface connection. The slide scanner scans a slide to obtain a histological image data set which is a WSI of the sample. The WSI is then stored in a digital file as a so-called virtual slide.

Step S91 provides the image data file containing image data of a WSI, as generated by a slide scanner. It will be appreciated the image data file may include multiple images, e.g. one for each of a plurality of stains, or one for each of a different depth in the sample (a so-called z-stack) obtained by stepping the focal plane of the microscope through a transparent or semi-transparent sample of finite depth. The image data file may also include multiple images from adjacent sample slices, each stained differently.

Step S92 is an optional step where some CNN pre-processing may be performed, as described by way of example further above, such as variance-based analysis, adaptive thresholding, morphological operations and so forth. In this step, some compression may also be carried out, e.g. in respect of areas identified by the pre-processing as not being relevant, e.g. non-tissue areas by which we mean areas of the slide where no sample was present.

Step S93 runs the above-described CNN, in particular as described with reference to Steps S51 to S54 of FIG. 4. A pixel-by-pixel classification of tissue type is performed to mark pixels of interest, followed by segmentation to outline areas of interest. For the segmentation, it is generally the case that contiguous of-interest pixels, i.e. ones that are touching each other or in close proximity to each other, belong to a common area of interest. More complex segmentation criteria will however usually be included to improve reliability, e.g. to identify two touching areas of interest with different pixel classifications, e.g. associated with two different of-interest classifications. The CNN assigns each pixel a probability.

In Step S94, the data generated by the area-of-interest-finding CNN in Step 73, i.e. the area-of-interest-specific data, is used to compute a set of summary statistics for each area of interest. For example, for each area of interest, a score may be computed as the mathematical average of the above-mentioned probability values for all the pixels contained in that area of interest. Some other summary statistic such as median, weighted average, etc. may also be used to compute a score. The set of summary statistics may include for example dimensional or morphological attributes of an area of interest, such as total area as measured by the number of pixels or shape of the area of interest, or prevalence of a certain pixel classification when there are multiple of-interest pixel classes. Areas of interest are not necessarily from a single slide; they may belong to separate slides, e.g. the tissue samples of two slides may be stained with different stains and thus highlight different classes of tumor cells, so that some areas of interest are associated with a first slide and other areas of interest with a second slide. In other implementations, the score can be computed using traditional image processing techniques applied to the areas of interest identified by the CNN. For example, shape and texture measures can be used to create a set of statistical measures to include in the summary statistics. Optionally Step S94 additionally carries out a filtering of the areas of interest based on the summary statistics. For example, the filter, which may be configured by the pathologist or be pre-set, may choose to pass only areas of interest with a maximum dimension above a threshold value, e.g. 100 micrometers.

Step S95 takes the set of areas of interest passed by Step S94 and ranks them in order. A ranking of the areas of interest can then be carried out based on the summary statistics and applying a set of criteria. Pre-sets of standard ranking approaches may be provided to the user, allowing the user to select on the basis of the pre-sets. Moreover, the user may be provided with a user interface to define which criteria are to be applied. In the case of scalar valued criteria, e.g. based on a length dimension or area or an integer count (e.g. number of pixels), the user may set threshold values, or value ranges for these criteria. The ranking order may be based on a composite score, or be a simple single parameter ranking, e.g. based on a size parameter of the area of interest such as area or maximum dimension, or a morphological parameter such as aspect ratio.

Step S96 applies variable image compression to the histological image data set with a compression algorithm that preferentially compresses pixels outside the areas of interest to generate a compressed version of the histological image data set. The compressed version is then stored to the slide digital file, i.e. the record. The image compression algorithm applied to areas that are not of interest may be a lossless compression algorithm, such as PNG (Portable Network Graphics) or GIF (Graphics Interchange Format), or a lossy compression algorithm, such as LZW (Lempel-Ziv-Welch), JPEG, JPEG 2000, JPEG XR or PGF (Progressive Graphics File), or a compression algorithm which includes both lossy and lossless compression. In other embodiments, all of the image data set may be subject to compression, but different compression algorithms, or the same compression algorithm with different levels of compression, may be applied variably depending on the areas of interest. If there are separate not-of-interest classes for non-tissue areas and tissue areas that are not of clinical interest, then the most aggressive compression may be used for the non-tissue areas, whereas the not-of-interest tissue areas may be compressed to a lesser degree. Another option is to reserve lossless compression for areas of interest, and lossy compression for areas not of interest. A still further option is to treat margins around areas of interest the same as areas of interest in respect of the compression, where the margin may be based on a thickness and be implemented by a blob dilation, or may be based on an integer number of image tiles, e.g. one or two image tiles are added to the perimeter of each area of interest.

For example, the JPEG format allows for a "quality" parameter to be customizable in the range 0 to 100, affecting how much data is discarded and the overall compression ratio. By having extra information from the interest classification performed by the CNN, this extra information identifying areas of interest and optionally level of interest can be used to decide how to vary the quality parameter. Namely, a lower quality (higher compression ratio) can be set to areas that are not of interest, or of lower interest, whereas a higher quality (lower compression ratio) or no compression or only lossless compression can be applied to areas deemed to be of interest, or high interest, by the CNN.

Memory space saving may be important, bearing in mind that uncompressed virtual slide data sets can be vast and as technical capabilities improve may become even larger. For example, a current slide scanner may generate virtual slides of a size of, for example, 20 to 50 GB for a single image, where a single image may be, for example be composed of 150,000×75,000 pixels. The compressed version of the histological image data set may be stored to the record by overwriting the histological image data set from which it has been compressed. Alternatively, the original raw image may be retained, but perhaps be routinely hidden, so that a user by default is given access to the compressed version when accessing a slide library.

Figure 8:
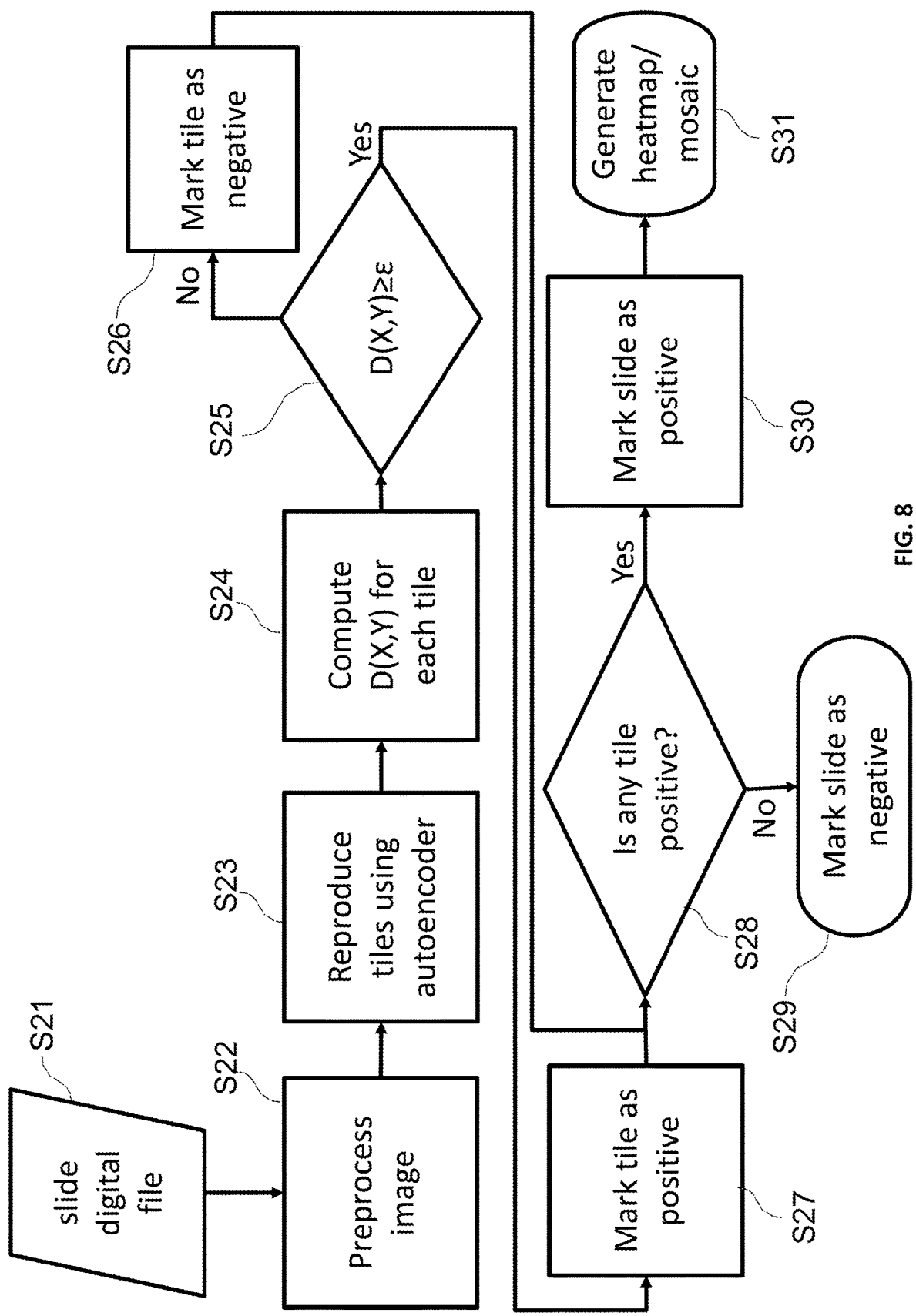
FIG. 8 is a flow diagram showing the steps involved in applying the trained autoencoder CNN to detect anomalies.

FIG. 8 is a flow diagram showing how the trained autoencoder (previously described in the alternative autoencoder training embodiment of FIG. 3) can be used to detect tissue that is anomalous and hence potentially toxically damaged, or at least changed, by a test compound.

Step S21 provides an image data file retrieved from a record stored in a data repository, such as a virtual slide library. The image data file is of a histological WSI, as may have been generated by a slide scanner. The histological image is of a tissue sample that has been treated with a test compound. The histological image comprises a two-dimensional array of pixels. It will be appreciated the image data file may include multiple images, e.g. one for each of a plurality of stains, or one for each of a different depth in the sample (a so-called z-stack) obtained by stepping the focal plane of the microscope through a transparent or semi-transparent sample of finite depth.

Step S22 is an optional step where some CNN preprocessing may be performed, as described by way of example further above, such as variance-based analysis, adaptive thresholding, morphological operations and so forth.

Step S23 uses an autoencoder that has been trained with a training data set as described above using tissue that has not been treated with the test compound. The autoencoder is applied to the histological image on a tile-by-tile basis with the aim of faithfully reproducing the input tiles as output tiles. The input tiles supplied to the autoencoder for anomaly detection are conveniently made the same size as the image tiles previously used for the self-supervised training the autoencoder.

Step S24 computes the distance D(X, Y) between the input and output patches of each tile.

Step S25 compares the distance 'D' to a threshold value 'ε'.

Step S26 marks the tile as negative, i.e. normal or non-toxic, if D (X, Y)<ε, whereas Step S27 marks the tile as positive, i.e. abnormal or toxic, if D (X, Y)≥ε. Each tile is thus marked with a binary label. The threshold value can be set by a user. For example, the visualization application may be provided with a user control by which the user can set the threshold value. Allowing the user to modify the threshold permits the user to increase or decrease sensitivity or specificity as desired.

Step S28 is arranged in the process flow after all tiles of a given image have been checked by steps S24 to S27 to test whether the image as a whole, i.e. the WSI, is negative or positive, following which the WSI is labelled negative or positive in Steps S29 and S30 respectively. The WSI negative or positive outcome is thus an overall toxicity label for the WSI (and its underlying record of which the WSI forms a part). The overall toxicity label is thus a binary label designating the histological image either as toxic/abnormal if any one of the image tiles has been determined to be positive and non-toxic/normal if none of the image tiles has been determined to be positive, i.e. all of the image tiles have been determined to be negative.

Step S31 generates a toxicity map for the histological image based on the computed distances that can, for example, be overlaid on the histological image in a composite display, either directly or after saving to the record as metadata associated with the image. The binary tile labels generated as the outcome of the test at Step S25 collectively constitute a binary mask for the image, wherein this binary mark may be the above-referred-to toxicity map. The distance values for each tile collectively constitute a scalar-valued mask for the image, wherein this scalar-valued mask is another option for the toxicity map. Such a scalar-valued mask can be, for example, overlaid on the image in a composite display as a heat map. In a visualization, the heat map could be presented with a color scale, or with contour lines for example. The distance values may be further processed for the heat map to provide a desired overlay presentation. For example, the distance values may be used as temperature values in the heat map unchanged, or merely scaled by a common conversion factor. Another possibility is that the toxicity map sets all below-threshold distance values to zero temperature, or some other constant value, so that when the heatmap is displayed the normal tissue areas are uniformly shown, e.g. not marked at all, or covered in a light gray wash.

Instead of retaining the distance values as scalar values in the heat map, they may be converted to discrete values that are in some way proportional to the distance value to provide a plurality of toxicity levels for the heat map, for example 2, 3, 4, 5 or more. Another option for the toxicity map is to apply a segmentation algorithm to group toxic tiles into toxic areas and thereby generate a segmentation mask of the toxic areas which can be stored separately from the tile-by-tile toxicity data or in place of it, since it will contain the same information content.

A still further option is to rank the toxic tiles, or toxic areas, according to toxicity as measured by the distances (or some other value derived therefrom in the course of further processing the distance values as described above), or aggregate distances in the case of toxic areas. The ranking data can be stored as metadata with or as part of the toxicity map.

There are various options for how a visualization application can utilize the toxicity map to create a visualization of the histological image which presents the abnormality data from the autoencoder in a way that is useful for a toxicological pathologist or other user.

The visualization may present an overview viewing pane in which the toxicity map is overlaid on the histological image, as already mentioned. Optionally, ranking label for toxic areas may be included, so that the pathologist can review the highest ranked area first, for example. Instead of an overlay, the toxicity map and the histological image could be presented adjacent each other, e.g. side-by-side, for one-to-one comparison. Usefully, the visualization application may be provided with a user interface control operable to permit a user to interact with the visualization so as to select a toxic area or individual toxic tile.

One form of visualization is a split screen in which one part of the screen shows an overview viewing pane and another part of the screen shows in a close-up viewing pane the currently selected toxic area at a higher magnification, for example with the native resolution of the underlying image data. If the individual toxic tiles, or toxic areas, are ranked by distance value, or aggregate distance value (or some value derived therefrom), then the visualization application may be provided with a user interface control operable to allow a user to scroll through the toxic tiles or areas in order of ranking, where the scroll may be upwards or downwards in ranking, for example as may be accessed by a mouse scroll wheel.

Another form of visualization is for the toxic tiles or areas to be presented in tabular or list form in order of ranking, with each ranking representing one row and each row including a thumbnail image of the toxic tile or area.

A still further form of visualization is for the toxic tiles or areas to be presented as a mosaic of images, so that the user is substantially only presented with the abnormal, i.e. toxic, parts of the image, and the normal areas are not displayed, or only peripherally displayed.

Example Embodiment

In one embodiment, a method employed by computer-automated system for processing a histological image of a tissue sample that has been treated with a test compound begins with receiving the histological image of the tissue sample, the histological image including a two-dimensional array of pixels. Next, the system applies a first convolutional neural network to the histological image to generate a first output image patch with a two-dimensional array of pixels with a mapping to that of the histology image. The first output image patch is generated by assigning one of a plurality of relevance classes to each pixel, wherein the plurality of relevance classes includes at least one class representing a pixel of interest and at least one class representing a pixel that is not of interest. Advantageously, the first convolutional neural network has been trained using a training data set comprising histological images and pathologist interaction data, wherein the pathologist interaction data has recorded a plurality of parameters relating to how pathologists have interacted with visualizations of histological images. Next, the system generates an area of interest map from the first output image patch. The area of interest map identifies areas of interest occupied by pixels of interest.

Next, a second convolutional neural network is applied to the histological image to generate a second output image patch with a two-dimensional array of pixels with a mapping to that of the histology image. In this case, the second convolutional network has been trained with a training data set comprising a plurality of histological images of tissue samples that have not been treated with the test compound. The system subsequently computes a distance between the second output image patch and the corresponding portion of the histological image in accordance with the mapping. Then the system generates a toxicity map for the histological image based on the computed distances and analyzes the area of interest map and the toxicity map to identify areas of the histological image that appear in both the area of interest map and the toxicity map. Finally, the system increases a toxicity confidence score for each area of the histological image that appears in both the area of interest map and the toxicity map.

Cnn Computing Platform

The proposed image processing may be carried out on a variety of computing architectures, in particular ones that are optimized for neural networks, which may be based on CPUs, GPUs, TPUs, FPGAs and/or ASICs. In some embodiments, the neural network is implemented using Google's Tensorflow software library running on Nvidia GPUs from Nvidia Corporation, Santa Clara, California, such as the Tesla K80 GPU. In other embodiments, the neural network can run on generic CPUs. Faster processing can be obtained by a purpose-designed processor for performing CNN calculations, for example the TPU disclosed in Jouppi et al 2017, the full contents of which is incorporated herein by reference.

Figure 9:
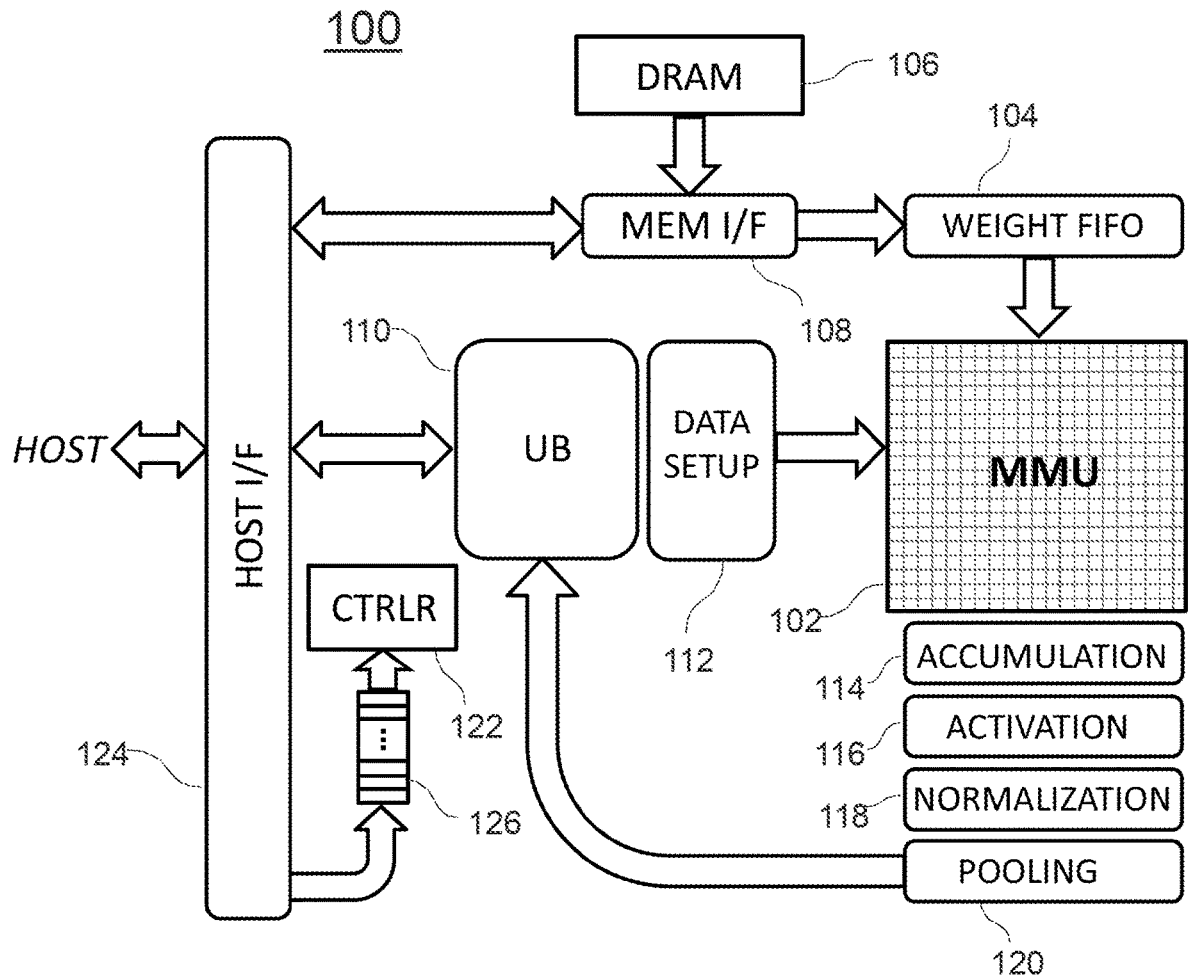
FIG. 9 is a block diagram of a TPU which may be used for performing the computations involved in implementing the neural network architecture of FIGS. 5A and 5B.

FIG. 9 shows the TPU of Jouppi et al 2017, being a simplified reproduction of Jouppi's FIG. 1. The TPU 100 has a systolic matrix multiplication unit (MMU) 102 which contains 256×256 MACs that can perform 8-bit multiply-and-adds on signed or unsigned integers. The weights for the MMU are supplied through a weight FIFO buffer 104 that in turn reads the weights from a memory 106, in the form of an off-chip 8 GB DRAM, via a suitable memory interface 108. A unified buffer (UB) 110 is provided to store the intermediate results. The MMU 102 is connected to receives inputs from the weight FIFO interface 104 and the UB 110 (via a systolic data setup unit 112) and outputs the 16-bit products of the MMU processing to an accumulator unit 114. An activation unit 116 performs nonlinear functions on the data held in the accumulator unit 114. After further processing by a normalizing unit 118 and a pooling unit 120, the intermediate results are sent to the UB 110 for resupply to the MMU 102 via the data setup unit 112. The pooling unit 120 may perform maximum pooling (i.e. maxpooling) or average pooling as desired. A programmable DMA controller 122 transfers data to or from the TPU's host computer and the UB 110. The TPU instructions are sent from the host computer to the controller 122 via a host interface 124 and an instruction buffer 126.

It will be understood that the computing power used for running the neural network, whether it be based on CPUs, GPUs or TPUs, may be hosted locally in a clinical network, e.g. the one described below, or remotely in a data center.

Network & Computing & Scanning Environment

The proposed computer-automated method operates in the context of a laboratory information system (LIS) which in turn is typically part of a larger clinical network environment, such as a hospital information system (HIS) or picture archiving and communication system (PACS). In the LIS, the WSIs will be retained in a database, typically a patient information database containing the electronic medical records of individual patients. The WSIs will be taken from stained tissue samples mounted on slides, the slides bearing printed barcode labels by which the WSIs are tagged with suitable metadata, since the microscopes acquiring the WSIs are equipped with barcode readers. From a hardware perspective, the LIS will be a conventional computer network, such as a local area network (LAN) with wired and wireless connections as desired.

Figure 10:
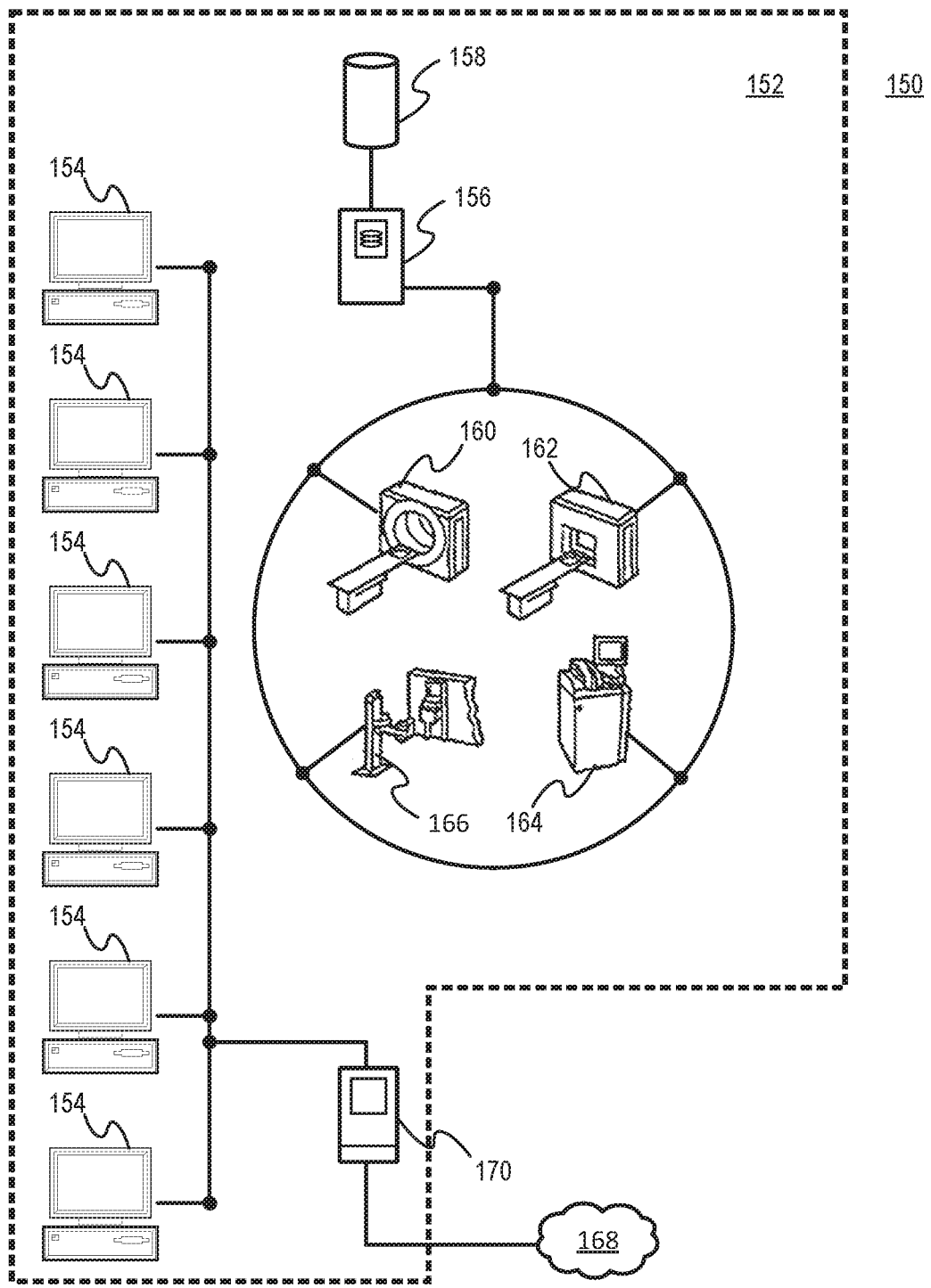
FIG. 10 shows an example computer network which can be used in conjunction with embodiments of the invention.

FIG. 10 shows an example computer network which can be used in conjunction with embodiments of the invention. The network 150 comprises a LAN in a hospital 152. The hospital 152 is equipped with a number of workstations 154 which each have access, via the local area network, to a hospital computer server 156 having an associated storage device 158. A LIS, HIS or PACS archive is stored on the storage device 158 so that data in the archive can be accessed from any of the workstations 154. One or more of the workstations 154 has access to a graphics card and to software for computer-implementation of methods of generating images as described hereinbefore. The software may be stored locally at the or each workstation 154 or may be stored remotely and downloaded over the network 150 to a workstation 154 when needed. In other example, methods embodying the invention may be executed on the computer server with the workstations 154 operating as terminals. For example, the workstations may be configured to receive user input defining a desired histological image data set and to display resulting images while CNN analysis is performed elsewhere in the system. Also, a number of histological and other medical imaging devices 160, 162, 164, 166 are connected to the hospital computer server 156. Image data collected with the devices 160, 162, 164, 166 can be stored directly into the LIS, HIS or PACS archive on the storage device 156. Thus, histological images can be viewed and processed immediately after the corresponding histological image data are recorded. The local area network is connected to the Internet 168 by a hospital Internet server 170, which allows remote access to the LIS, HIS or PACS archive. This is of use for remote accessing of the data and for transferring data between hospitals, for example, if a patient is moved, or to allow external research to be undertaken.

Figure 11:
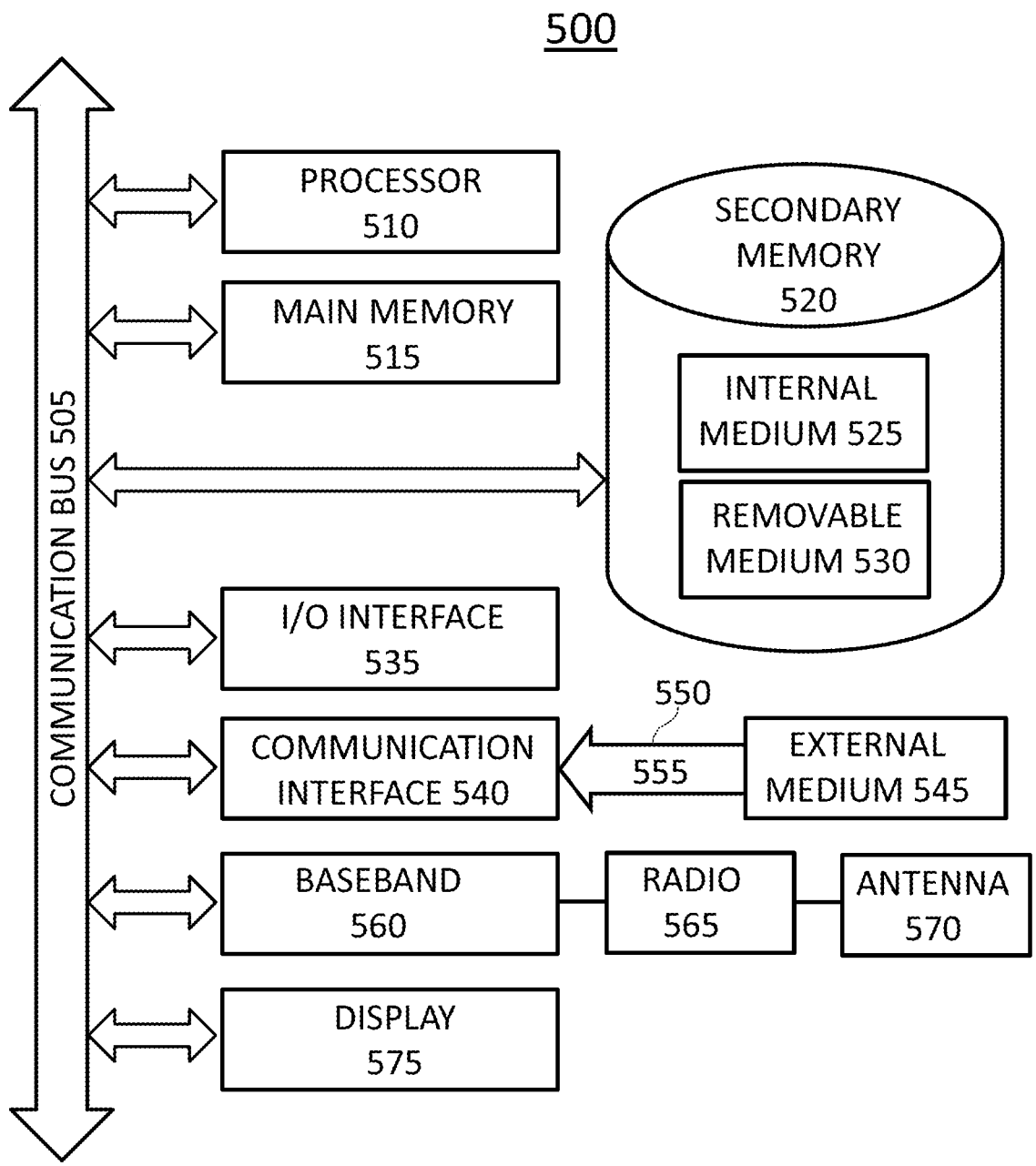
FIG. 11 is a block diagram of a computing apparatus that may be used for example as the host computer for the TPU of FIG. 9.

FIG. 11 is a block diagram illustrating an example computing apparatus 500 that may be used in connection with various embodiments described herein. For example, computing apparatus 500 may be used as a computing node in the above-mentioned LIS or PACS system, for example a host computer from which CNN processing is carried out in conjunction with a suitable GPU, or the TPU shown in FIG. 9.

Computing apparatus 500 can be a server or any conventional personal computer, or any other processor-enabled device that is capable of wired or wireless data communication. Other computing apparatus, systems and/or architectures may be also used, including devices that are not capable of wired or wireless data communication, as will be clear to those skilled in the art.

Computing apparatus 500 preferably includes one or more processors, such as processor 510. The processor 510 may be for example a CPU, GPU, TPU or arrays or combinations thereof such as CPU and TPU combinations or CPU and GPU combinations. Additional processors may be provided, such as an auxiliary processor to manage input/output, an auxiliary processor to perform floating point mathematical operations (e.g. a TPU), a special-purpose microprocessor having an architecture suitable for fast execution of signal processing algorithms (e.g., digital signal processor, image processor), a slave processor subordinate to the main processing system (e.g., back-end processor), an additional microprocessor or controller for dual or multiple processor systems, or a coprocessor. Such auxiliary processors may be discrete processors or may be integrated with the processor 510. Examples of CPUs which may be used with computing apparatus 500 are, the Pentium processor, Core i7 processor, and Xeon processor, all of which are available from Intel Corporation of Santa Clara, California. An example GPU which may be used with computing apparatus 500 is Tesla K80 GPU of Nvidia Corporation, Santa Clara, California.

Processor 510 is connected to a communication bus 505. Communication bus 505 may include a data channel for facilitating information transfer between storage and other peripheral components of computing apparatus 500. Communication bus 505 further may provide a set of signals used for communication with processor 510, including a data bus, address bus, and control bus (not shown). Communication bus 505 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

Computing apparatus 500 preferably includes a main memory 515 and may also include a secondary memory 520. Main memory 515 provides storage of instructions and data for programs executing on processor 510, such as one or more of the functions and/or modules discussed above. It should be understood that computer readable program instructions stored in the memory and executed by processor 510 may be assembler instructions, instruction-set-architecture (ISA) instructions, machine instructions, machine dependent instructions, microcode, firmware instructions, state-setting data, configuration data for integrated circuitry, or either source code or object code written in and/or compiled from any combination of one or more programming languages, including without limitation Smalltalk, C/C++, Java, JavaScript, Perl, Visual Basic, .NET, and the like. Main memory 515 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Secondary memory 520 may optionally include an internal memory 525 and/or a removable medium 530. Removable medium 530 is read from and/or written to in any well-known manner. Removable storage medium 530 may be, for example, a magnetic tape drive, a compact disc (CD) drive, a digital versatile disc (DVD) drive, other optical drive, a flash memory drive, etc.

Removable storage medium 530 is a non-transitory computer-readable medium having stored thereon computer-executable code (i.e., software) and/or data. The computer software or data stored on removable storage medium 530 is read into computing apparatus 500 for execution by processor 510.

The secondary memory 520 may include other similar elements for allowing computer programs or other data or instructions to be loaded into computing apparatus 500. Such means may include, for example, an external storage medium 545 and a communication interface 540, which allows software and data to be transferred from external storage medium 545 to computing apparatus 500. Examples of external storage medium 545 may include an external hard disk drive, an external optical drive, an external magneto-optical drive, etc. Other examples of secondary memory 520 may include semiconductor-based memory such as programmable read-only memory (PROM), erasable programmable read-only memory (EPROM), electrically erasable read-only memory (EEPROM), or flash memory (block-oriented memory similar to EEPROM).

As mentioned above, computing apparatus 500 may include a communication interface 540. Communication interface 540 allows software and data to be transferred between computing apparatus 500 and external devices (e.g. printers), networks, or other information sources. For example, computer software or executable code may be transferred to computing apparatus 500 from a network server via communication interface 540. Examples of communication interface 540 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 540 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 540 are generally in the form of electrical communication signals 555. These signals 555 may be provided to communication interface 540 via a communication channel 550. In an embodiment, communication channel 550 may be a wired or wireless network, or any variety of other communication links. Communication channel 550 carries signals 555 and can be implemented using a variety of wired or wireless communication means including wire or cable, fiber optics, conventional phone line, cellular phone link, wireless data communication link, radio frequency ("RF") link, or infrared link, just to name a few.

Computer-executable code (i.e., computer programs or software) is stored in main memory 515 and/or the secondary memory 520. Computer programs can also be received via communication interface 540 and stored in main memory 515 and/or secondary memory 520. Such computer programs, when executed, enable computing apparatus 500 to perform the various functions of the disclosed embodiments as described elsewhere herein.

In this document, the term "computer-readable medium" is used to refer to any non-transitory computer-readable storage media used to provide computer-executable code (e.g., software and computer programs) to computing apparatus 500. Examples of such media include main memory 515, secondary memory 520 (including internal memory 525, removable medium 530, and external storage medium 545), and any peripheral device communicatively coupled with communication interface 540 (including a network information server or other network device). These non-transitory computer-readable media are means for providing executable code, programming instructions, and software to computing apparatus 500. In an embodiment that is implemented using software, the software may be stored on a computer-readable medium and loaded into computing apparatus 500 by way of removable medium 530, I/O interface 535, or communication interface 540. In such an embodiment, the software is loaded into computing apparatus 500 in the form of electrical communication signals 555. The software, when executed by processor 510, preferably causes processor 510 to perform the features and functions described elsewhere herein.

I/O interface 535 provides an interface between one or more components of computing apparatus 500 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

Computing apparatus 500 also includes optional wireless communication components that facilitate wireless communication over a voice network and/or a data network. The wireless communication components comprise an antenna system 570, a radio system 565, and a baseband system 560. In computing apparatus 500, radio frequency (RF) signals are transmitted and received over the air by antenna system 570 under the management of radio system 565.

Antenna system 570 may comprise one or more antennae and one or more multiplexors (not shown) that perform a switching function to provide antenna system 570 with transmit and receive signal paths. In the receive path, received RF signals can be coupled from a multiplexor to a low noise amplifier (not shown) that amplifies the received RF signal and sends the amplified signal to radio system 565.

Radio system 565 may comprise one or more radios that are configured to communicate over various frequencies. In an embodiment, radio system 565 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 565 to baseband system 560.

If the received signal contains audio information, then baseband system 560 decodes the signal and converts it to an analog signal. Then the signal is amplified and sent to a speaker. Baseband system 560 also receives analog audio signals from a microphone. These analog audio signals are converted to digital signals and encoded by baseband system 560. Baseband system 560 also codes the digital signals for transmission and generates a baseband transmit audio signal that is routed to the modulator portion of radio system 565. The modulator mixes the baseband transmit audio signal with an RF carrier signal generating an RF transmit signal that is routed to antenna system 570 and may pass through a power amplifier (not shown). The power amplifier amplifies the RF transmit signal and routes it to antenna system 570 where the signal is switched to the antenna port for transmission.

Baseband system 560 is also communicatively coupled with processor 510, which may be a central processing unit (CPU). Processor 510 has access to data storage areas 515 and 520. Processor 510 is preferably configured to execute instructions (i.e., computer programs or software) that can be stored in main memory 515 or secondary memory 520. Computer programs can also be received from baseband processor 560 and stored in main memory 510 or in secondary memory 520 or executed upon receipt. Such computer programs, when executed, enable computing apparatus 500 to perform the various functions of the disclosed embodiments. For example, data storage areas 515 or 520 may include various software modules.

The computing apparatus further comprises a display 575 directly attached to the communication bus 505 which may be provided instead of or addition to any display connected to the I/O interface 535 referred to above.

Various embodiments may also be implemented primarily in hardware using, for example, components such as application specific integrated circuits (ASICs), programmable logic arrays (PLA), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A computer readable storage medium, as referred to herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The illustrated flowcharts and block diagrams illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Apparatus and methods embodying the invention are capable of being hosted in and delivered by a cloud computing environment. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (Saas): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls). Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

It will be clear to one skilled in the art that many improvements and modifications can be made to the foregoing exemplary embodiment without departing from the scope of the present disclosure.

Figure 12A:
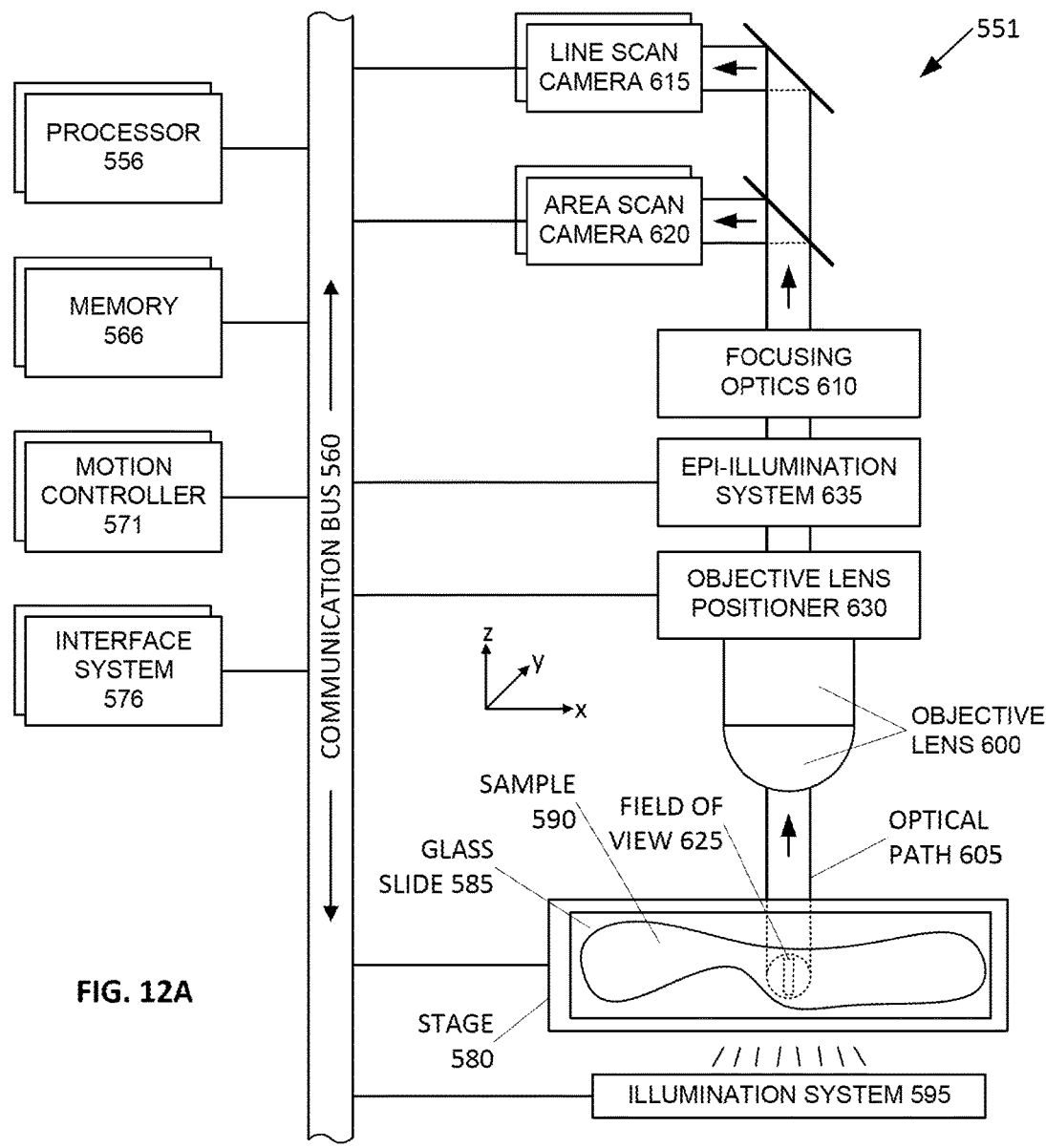
FIG. 12A is a block diagram illustrating an example processor enabled device 550 that may be used in connection with various embodiments described herein.

FIG. 12A is a block diagram illustrating an example processor enabled device 551 that may be used in connection with various embodiments described herein. Alternative forms of the device 551 may also be used as will be understood by the skilled artisan. In the illustrated embodiment, the device 551 is presented as a digital imaging device (also referred to herein as a scanner system or a scanning system) that comprises one or more processors 556, one or more memories 566, one or more motion controllers 571, one or more interface systems 576, one or more movable stages 580 that each support one or more glass slides 585 with one or more samples 590, one or more illumination systems 595 that illuminate the sample, one or more objective lenses 600 that each define an optical path 605 that travels along an optical axis, one or more objective lens positioners 630, one or more optional epi-illumination systems 635 (e.g., included in a fluorescence scanner system), one or more focusing optics 610, one or more line scan cameras 615 and/or one or more area scan cameras 620, each of which define a separate field of view 625 on the sample 590 and/or glass slide 585. The various elements of the scanner system 551 are communicatively coupled via one or more communication busses 560. Although there may be one or more of each of the various elements of the scanner system 551, for simplicity in the description that follows, these elements will be described in the singular except when needed to be described in the plural to convey the appropriate information.

The one or more processors 556 may include, for example, a central processing unit ("CPU") and a separate graphics processing unit ("GPU") capable of processing instructions in parallel or the one or more processors 556 may include a multicore processor capable of processing instructions in parallel. Additional separate processors may also be provided to control particular components or perform particular functions such as image processing. For example, additional processors may include an auxiliary processor to manage data input, an auxiliary processor to perform floating point mathematical operations, a special-purpose processor having an architecture suitable for fast execution of signal processing algorithms (e.g., digital signal processor), a slave processor subordinate to the main processor (e.g., back-end processor), an additional processor for controlling the line scan camera 615, the stage 580, the objective lens 225, and/or a display (not shown). Such additional processors may be separate discrete processors or may be integrated with the processor 556.

The memory 566 provides storage of data and instructions for programs that can be executed by the processor 556. The memory 566 may include one or more volatile and persistent computer-readable storage mediums that store the data and instructions, for example, a random access memory, a read only memory, a hard disk drive, removable storage drive, and the like. The processor 556 is configured to execute instructions that are stored in memory 566 and communicate via communication bus 560 with the various elements of the scanner system 551 to carry out the overall function of the scanner system 551.

The one or more communication busses 560 may include a communication bus 560 that is configured to convey analog electrical signals and may include a communication bus 560 that is configured to convey digital data. Accordingly, communications from the processor 556, the motion controller 571, and/or the interface system 576 via the one or more communication busses 560 may include both electrical signals and digital data. The processor 556, the motion controller 571, and/or the interface system 576 may also be configured to communicate with one or more of the various elements of the scanning system 551 via a wireless communication link.

The motion control system 571 is configured to precisely control and coordinate XYZ movement of the stage 580 and the objective lens 600 (e.g., via the objective lens positioner 630). The motion control system 571 is also configured to control movement of any other moving part in the scanner system 551. For example, in a fluorescence scanner embodiment, the motion control system 571 is configured to coordinate movement of optical filters and the like in the epi-illumination system 635.

The interface system 576 allows the scanner system 551 to interface with other systems and human operators. For example, the interface system 576 may include a user interface to provide information directly to an operator and/or to allow direct input from an operator. The interface system 576 is also configured to facilitate communication and data transfer between the scanning system 551 and one or more external devices that are directly connected (e.g., a printer, removable storage medium) or external devices such as an image server system, an operator station, a user station, and an administrative server system that are connected to the scanner system 551 via a network (not shown).

The illumination system 595 is configured to illuminate a portion of the sample 590. The illumination system may include, for example, a light source and illumination optics. The light source could be a variable intensity halogen light source with a concave reflective mirror to maximize light output and a KG-1 filter to suppress heat. The light source could also be any type of arc-lamp, laser, or other source of light. In one embodiment, the illumination system 595 illuminates the sample 590 in transmission mode such that the line scan camera 615 and/or area scan camera 620 sense optical energy that is transmitted through the sample 590. Alternatively, or in combination, the illumination system 595 may also be configured to illuminate the sample 590 in reflection mode such that the line scan camera 615 and/or area scan camera 620 sense optical energy that is reflected from the sample 590. Overall, the illumination system 595 is configured to be suitable for interrogation of the microscopic sample 590 in any known mode of optical microscopy.

In one embodiment, the scanner system 551 optionally includes an epi-illumination system 635 to optimize the scanner system 551 for fluorescence scanning. Fluorescence scanning is the scanning of samples 590 that include fluorescence molecules, which are photon sensitive molecules that can absorb light at a specific wavelength (excitation). These photon sensitive molecules also emit light at a higher wavelength (emission). Because the efficiency of this photoluminescence phenomenon is very low, the amount of emitted light is often very low. This low amount of emitted light typically frustrates conventional techniques for scanning and digitizing the sample 590 (e.g., transmission mode microscopy). Advantageously, in an optional fluorescence scanner system embodiment of the scanner system 551, use of a line scan camera 615 that includes multiple linear sensor arrays (e.g., a time delay integration ("TDI") line scan camera) increases the sensitivity to light of the line scan camera by exposing the same area of the sample 590 to each of the multiple linear sensor arrays of the line scan camera 615. This is particularly useful when scanning faint fluorescence samples with low emitted light.

Accordingly, in a fluorescence scanner system embodiment, the line scan camera 615 is preferably a monochrome TDI line scan camera. Advantageously, monochrome images are ideal in fluorescence microscopy because they provide a more accurate representation of the actual signals from the various channels present on the sample. As will be understood by those skilled in the art, a fluorescence sample 590 can be labeled with multiple florescence dyes that emit light at different wavelengths, which are also referred to as "channels."

Furthermore, because the low and high end signal levels of various fluorescence samples present a wide spectrum of wavelengths for the line scan camera 615 to sense, it is desirable for the low and high end signal levels that the line scan camera 615 can sense to be similarly wide. Accordingly, in a fluorescence scanner embodiment, a line scan camera 615 used in the fluorescence scanning system 551 is a monochrome 10 bit 64 linear array TDI line scan camera. It should be noted that a variety of bit depths for the line scan camera 615 can be employed for use with a fluorescence scanner embodiment of the scanning system 551.

The movable stage 580 is configured for precise XY movement under control of the processor 556 or the motion controller 571. The movable stage may also be configured for movement in Z under control of the processor 556 or the motion controller 571. The moveable stage is configured to position the sample in a desired location during image data capture by the line scan camera 615 and/or the area scan camera. The moveable stage is also configured to accelerate the sample 590 in a scanning direction to a substantially constant velocity and then maintain the substantially constant velocity during image data capture by the line scan camera 615. In one embodiment, the scanner system 551 may employ a high precision and tightly coordinated XY grid to aid in the location of the sample 590 on the movable stage 580. In one embodiment, the movable stage 580 is a linear motor based XY stage with high precision encoders employed on both the X and the Y axis. For example, very precise nanometer encoders can be used on the axis in the scanning direction and on the axis that is in the direction perpendicular to the scanning direction and on the same plane as the scanning direction. The stage is also configured to support the glass slide 585 upon which the sample 590 is disposed.

The sample 590 can be anything that may be interrogated by optical microscopy. For example, a glass microscope slide 585 is frequently used as a viewing substrate for specimens that include tissues and cells, chromosomes, DNA, protein, blood, bone marrow, urine, bacteria, beads, biopsy materials, or any other type of biological material or substance that is either dead or alive, stained or unstained, labeled or unlabeled. The sample 590 may also be an array of any type of DNA or DNA-related material such as cDNA or RNA or protein that is deposited on any type of slide or other substrate, including any and all samples commonly known as a microarrays. The sample 590 may be a microtiter plate, for example a 96-well plate. Other examples of the sample 590 include integrated circuit boards, electrophoresis records, petri dishes, film, semiconductor materials, forensic materials, or machined parts.

Objective lens 600 is mounted on the objective positioner 630 which, in one embodiment, may employ a very precise linear motor to move the objective lens 600 along the optical axis defined by the objective lens 600. For example, the linear motor of the objective lens positioner 630 may include a 50 nanometer encoder. The relative positions of the stage 580 and the objective lens 600 in XYZ axes are coordinated and controlled in a closed loop manner using motion controller 571 under the control of the processor 556 that employs memory 566 for storing information and instructions, including the computer-executable programmed steps for overall scanning system 551 operation.

In one embodiment, the objective lens 600 is a plan apochromatic ("APO") infinity corrected objective with a numerical aperture corresponding to the highest spatial resolution desirable, where the objective lens 600 is suitable for transmission mode illumination microscopy, reflection mode illumination microscopy, and/or epi-illumination mode fluorescence microscopy (e.g., an Olympus 40×, 0.75NA or 20X, 0.75 NA). Advantageously, objective lens 600 is capable of correcting for chromatic and spherical aberrations. Because objective lens 600 is infinity corrected, focusing optics 610 can be placed in the optical path 605 above the objective lens 600 where the light beam passing through the objective lens becomes a collimated light beam. The focusing optics 610 focus the optical signal captured by the objective lens 600 onto the light-responsive elements of the line scan camera 615 and/or the area scan camera 620 and may include optical components such as filters, magnification changer lenses, etc. The objective lens 600 combined with focusing optics 610 provides the total magnification for the scanning system 551. In one embodiment, the focusing optics 610 may contain a tube lens and an optional 2× magnification changer. Advantageously, the 2× magnification changer allows a native 20× objective lens 600 to scan the sample 590 at 40× magnification.

The line scan camera 615 comprises at least one linear array of picture elements ("pixels"). The line scan camera may be monochrome or color. Color line scan cameras typically have at least three linear arrays, while monochrome line scan cameras may have a single linear array or plural linear arrays. Any type of singular or plural linear array, whether packaged as part of a camera or custom-integrated into an imaging electronic module, can also be used. For example, 3 linear array ("red-green-blue" or "RGB") color line scan camera or a 96 linear array monochrome TDI may also be used. TDI line scan cameras typically provide a substantially better signal-to-noise ratio ("SNR") in the output signal by summing intensity data from previously imaged regions of a specimen, yielding an increase in the SNR that is in proportion to the square-root of the number of integration stages. TDI line scan cameras comprise multiple linear arrays, for example, TDI line scan cameras are available with 24, 32, 48, 64, 96, or even more linear arrays. The scanner system 551 also supports linear arrays that are manufactured in a variety of formats including some with 512 pixels, some with 1024 pixels, and others having as many as 4096 pixels. Similarly, linear arrays with a variety of pixel sizes can also be used in the scanner system 551. The salient requirement for the selection of any type of line scan camera 615 is that the motion of the stage 580 can be synchronized with the line rate of the line scan camera 615 so that the stage 580 can be in motion with respect to the line scan camera 615 during the digital image capture of the sample 590.

The image data generated by the line scan camera 615 is stored a portion of the memory 566 and processed by the processor 556 to generate a contiguous digital image of at least a portion of the sample 590. The contiguous digital image can be further processed by the processor 556 and the revised contiguous digital image can also be stored in the memory 566.

In an embodiment with two or more line scan cameras 615, at least one of the line scan cameras 615 can be configured to function as a focusing sensor that operates in combination with at least one of the line scan cameras 615 that is configured to function as an imaging sensor. The focusing sensor can be logically positioned on the same optical axis as the imaging sensor or the focusing sensor may be logically positioned before or after the imaging sensor with respect to the scanning direction of the scanner system 551. In such an embodiment with at least one line scan camera 615 functioning as a focusing sensor, the image data generated by the focusing sensor is stored in a portion of the memory 566 and processed by the one or more processors 556 to generate focus information to allow the scanner system 551 to adjust the relative distance between the sample 590 and the objective lens 600 to maintain focus on the sample during scanning. Additionally, in one embodiment the at least one line scan camera 615 functioning as a focusing sensor may be oriented such that each of a plurality of individual pixels of the focusing sensor is positioned at a different logical height along the optical path 605.

In operation, the various components of the scanner system 551 and the programmed modules stored in memory 566 enable automatic scanning and digitizing of the sample 590, which is disposed on a glass slide 585. The glass slide 585 is securely placed on the movable stage 580 of the scanner system 551 for scanning the sample 590. Under control of the processor 556, the movable stage 580 accelerates the sample 590 to a substantially constant velocity for sensing by the line scan camera 615, where the speed of the stage is synchronized with the line rate of the line scan camera 615. After scanning a stripe of image data, the movable stage 580 decelerates and brings the sample 590 to a substantially complete stop. The movable stage 580 then moves orthogonal to the scanning direction to position the sample 590 for scanning of a subsequent stripe of image data, e.g., an adjacent stripe. Additional stripes are subsequently scanned until an entire portion of the sample 590 or the entire sample 590 is scanned.

For example, during digital scanning of the sample 590, a contiguous digital image of the sample 590 is acquired as a plurality of contiguous fields of view that are combined together to form an image strip. A plurality of adjacent image strips are similarly combined together to form a contiguous digital image of a portion or the entire sample 590. The scanning of the sample 590 may include acquiring vertical image strips or horizontal image strips. The scanning of the sample 590 may be either top-to-bottom, bottom-to-top, or both (bi-directional) and may start at any point on the sample. Alternatively, the scanning of the sample 590 may be either left-to-right, right-to-left, or both (bi-directional) and may start at any point on the sample. Additionally, it is not necessary that image strips be acquired in an adjacent or contiguous manner. Furthermore, the resulting image of the sample 590 may be an image of the entire sample 590 or only a portion of the sample 590.

In one embodiment, computer-executable instructions (e.g., programmed modules and software) are stored in the memory 566 and, when executed, enable the scanning system 551 to perform the various functions described herein. In this description, the term "computer-readable storage medium" is used to refer to any media used to store and provide computer executable instructions to the scanning system 551 for execution by the processor 556. Examples of these media include memory 566 and any removable or external storage medium (not shown) communicatively coupled with the scanning system 551 either directly or indirectly, for example via a network (not shown).

Figure 12B:
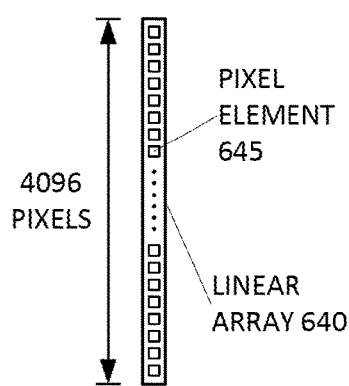
FIG. 12B is a block diagram illustrating an example line scan camera having a single linear array.

FIG. 12B illustrates a line scan camera having a single linear array 640, which may be implemented as a charge coupled device ("CCD") array. The single linear array 640 comprises a plurality of individual pixels 645. In the illustrated embodiment, the single linear array 640 has 4096 pixels. In alternative embodiments, linear array 640 may have more or fewer pixels. For example, common formats of linear arrays include 512, 1024, and 4096 pixels. The pixels 645 are arranged in a linear fashion to define a field of view 625 for the linear array 640. The size of the field of view varies in accordance with the magnification of the scanner system 551.

Figure 12C:
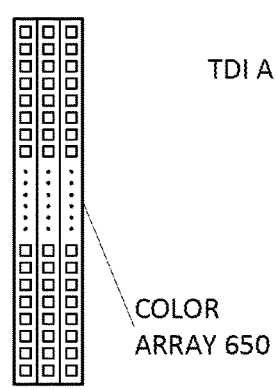
FIG. 12C is a block diagram illustrating an example line scan camera having three linear arrays.

FIG. 12C illustrates a line scan camera having three linear arrays, each of which may be implemented as a CCD array. The three linear arrays combine to form a color array 650. In one embodiment, each individual linear array in the color array 650 detects a different color intensity, for example red, green, or blue. The color image data from each individual linear array in the color array 650 is combined to form a single field of view 625 of color image data.

Figure 12D:
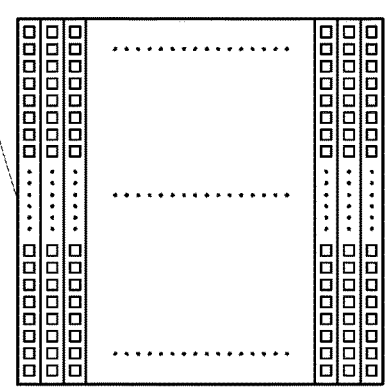
FIG. 12D is a block diagram illustrating an example line scan camera having a plurality of linear arrays.

FIG. 12D illustrates a line scan camera having a plurality of linear arrays, each of which may be implemented as a CCD array. The plurality of linear arrays combine to form a TDI array 655. Advantageously, a TDI line scan camera may provide a substantially better SNR in its output signal by summing intensity data from previously imaged regions of a specimen, yielding an increase in the SNR that is in proportion to the square-root of the number of linear arrays (also referred to as integration stages). A TDI line scan camera may comprise a larger variety of numbers of linear arrays, for example common formats of TDI line scan cameras include 24, 32, 48, 64, 96, 120 and even more linear arrays.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An apparatus comprising:
   a memory configured to store computer-executable instructions; and
   a hardware processor in communication with the memory, wherein the computer-executable instructions, when executed by the processor, configure the processor to:
   receive a histological image including a first two-dimensional array of pixels;
   generate, using a first convolutional neural network, a first output image mapped to the histological image and one of a plurality of relevance classes assigned to each pixel of the first output image, the first convolutional neural network being trained based on a training data set including (a) histological images and (b) pathologist interaction data, wherein the plurality of relevance classes includes at least one class representing a pixel of interest and at least one class representing a pixel that is not of interest, and wherein the pathologist interaction data comprise parameters relating to how pathologists have interacted with a plurality of other histological images; and
   generate from the first output image a segmentation mask in which areas of interest occupied by pixels of interest are marked;
   apply a second convolutional neural network to the histological image to generate a second output image with a second two-dimensional array of pixels with a mapping to that of the histology image, wherein the histological image is of a tissue sample that has been treated with a test compound, and wherein the second convolutional network has been trained with a training data set comprising a plurality of histological images of tissue samples that have not been treated with the test compound;
   compute a distance between the second output image and the corresponding portion of the histological image in accordance with the mapping;
   generate a toxicity map for the histological image based on the computed distances;
   analyze the segmentation map and the toxicity map to identify areas of the histological image that are marked as areas of interest in the segmentation map and that are identified as exhibiting toxicity in the toxicity map; and
   increase a toxicity confidence score for each area of the histological image that is marked as of interest in the segmentation map and is also identified as exhibiting toxicity in the toxicity map.

2. The apparatus of claim 1, further comprising:
   a visualization application operable to create visualizations of histological images having regard to their toxicity maps; and a display configured to receive visualizations from the visualization application.

3. The apparatus of claim 2, wherein the visualization application provides a user interface toxic area selection control operable to permit a user to interact with a visualization so as to select a toxic area.

4. The apparatus of claim 3, wherein the toxic area selection control has a scroll function for sweeping through the toxic areas in order of ranking.

5. The apparatus of claim 3, further comprising: a data repository configured to store records of patient data including histological images with associated toxicity maps; and network connections enabling transfer of patient data records or parts thereof between the computer apparatus and the data repository.

6. The apparatus of claim 1, wherein the computer-executable instructions, when executed, further configure the processor to identify one or more areas which are marked as of interest in the segmentation map and are also identified as exhibiting toxicity in the toxicity map as toxic.

7. The apparatus of claim 6, wherein the toxicity map includes a heat map in which areas identified as toxic are assigned a temperature value proportional to their distance value.

8. The apparatus of claim 7, wherein the computer-executable instructions, when executed, further configure the processor to apply a segmentation algorithm to the toxicity map to group areas identified as toxic and thereby generate a segmentation mask of toxic areas.

9. A method comprising:
receiving a histological image including a first two-dimensional array of pixels;
generating, using a first convolutional neural network, a first output image mapped to the histological image and one of a plurality of relevance classes assigned to each pixel of the first output image, the first convolutional neural network being trained based on a training data set including (a) histological images and (b) pathologist interaction data, wherein the plurality of relevance classes includes at least one class representing a pixel of interest and at least one class representing a pixel that is not of interest, and wherein the pathologist interaction data comprise parameters relating to how pathologists have interacted with a plurality of other histological images; and
generating from the first output image a segmentation mask in which areas of interest occupied by pixels of interest are marked;
applying a second convolutional neural network to the histological image to generate a second output image with a second two-dimensional array of pixels with a mapping to that of the histology image, wherein the histological image is of a tissue sample that has been treated with a test compound, and wherein the second convolutional network has been trained with a training data set comprising a plurality of histological images of tissue samples that have not been treated with the test compound;
computing a distance between the second output image and the corresponding portion of the histological image in accordance with the mapping;
generating a toxicity map for the histological image based on the computed distances;
analyzing the segmentation map and the toxicity map to identify areas of the histological image that are marked as areas of interest in the segmentation map and that are identified as exhibiting toxicity in the toxicity map; and
increasing a toxicity confidence score for each area of the histological image that is marked as of interest in the segmentation map and is also identified as exhibiting toxicity in the toxicity map.

10. The method of claim 9, wherein the method comprises identifying one or more areas which are marked as of interest in the segmentation map and are also identified as exhibiting toxicity in the toxicity map as toxic.

11. The method of claim 10, wherein the toxicity map includes a heat map in which areas identified as toxic are assigned a temperature value proportional to their distance value.

12. The method of claim 10, further comprising applying a segmentation algorithm to the toxicity map to group areas identified as toxic and thereby generate a second segmentation mask, wherein the second segmentation mask depicts toxic areas.

13. The method of claim 10, further comprising saving an overall toxicity label, wherein the overall toxicity label is a binary label designating the histological image as toxic if any area in the histological image has been identified as toxic and non-toxic if no area in the histological image has been identified as toxic.

14. The method of claim 9, further comprising:
providing a visualization application; and
creating a visualization of the histological image having regard to the toxicity map.

15. The method of claim 14, wherein the visualization includes an overview viewing pane in which the toxicity map is overlaid on the histological image.

16. The method of claim 14, wherein the visualization includes respective overview viewing panes in which the toxicity map and the histological image are presented adjacent each other for one-to-one comparison.

17. The method of claim 14, further comprising providing a user interface toxic area selection control operable to permit a user to interact with the visualization so as to select an area identified as toxic.

18. The method of claim 17 wherein the toxic area selection control has a scroll function for sweeping through toxic areas in order of ranking.

19. The method of claim 14, wherein the visualization application has a user control by which the user can set a threshold value used to identify areas as toxic.

20. The method of claim 14, wherein the visualization comprises a heat map presented with contour lines.

* * * * *